US009867376B2

(12) United States Patent
Almsick et al.

(10) Patent No.: US 9,867,376 B2
(45) Date of Patent: Jan. 16, 2018

(54) HERBICIDAL COMPOSITIONS COMPRISING N-TETRAZOL-5-YL)- OR N-(TRIAZOL-5-YL)ARYLCARBOXAMIDES

(71) Applicant: BAYER CROPSCIENCE AG, Monheim (DE)

(72) Inventors: Andreas Almsick, Karben (DE); Elmar Gatzweiler, Bad Nauheim (DE); Erwin Hacker, Langenenslingen (DE); Ralf Braun, Ramberg (DE); Hubert Menne, Mainz-Kastel (DE); Klaus Trabold, Heidelberg (DE); Christian Waldraff, Bad Vilbel (DE)

(73) Assignee: BAYER CROPSCIENCE AG, Monheim am Rhein (DE)

( * ) Notice: Subject to any disclaimer, the term of this patent is extended or adjusted under 35 U.S.C. 154(b) by 0 days.

(21) Appl. No.: 14/401,249

(22) PCT Filed: May 22, 2013

(86) PCT No.: PCT/EP2013/060468
§ 371 (c)(1),
(2) Date: Nov. 14, 2014

(87) PCT Pub. No.: WO2013/174845
PCT Pub. Date: Nov. 28, 2013

(65) Prior Publication Data
US 2015/0264933 A1   Sep. 24, 2015

(30) Foreign Application Priority Data
May 24, 2012  (EP) .................... 12169189

(51) Int. Cl.
| | | |
|---|---|---|
| *A01N 43/713* | (2006.01) | |
| *A01N 57/20* | (2006.01) | |
| *A01N 25/00* | (2006.01) | |
| *A01N 43/653* | (2006.01) | |
| *A01N 43/80* | (2006.01) | |
| *A01N 33/18* | (2006.01) | |
| *A01N 37/10* | (2006.01) | |
| *A01N 37/34* | (2006.01) | |
| *A01N 43/10* | (2006.01) | |
| *A01N 43/40* | (2006.01) | |
| *A01N 43/54* | (2006.01) | |
| *A01N 43/68* | (2006.01) | |
| *A01N 43/707* | (2006.01) | |
| *A01N 43/76* | (2006.01) | |
| *A01N 43/82* | (2006.01) | |
| *A01N 43/90* | (2006.01) | |
| *A01N 47/36* | (2006.01) | |

(52) U.S. Cl.
CPC ............ *A01N 57/20* (2013.01); *A01N 25/00* (2013.01); *A01N 33/18* (2013.01); *A01N 37/10* (2013.01); *A01N 37/34* (2013.01); *A01N 43/10* (2013.01); *A01N 43/40* (2013.01); *A01N 43/54* (2013.01); *A01N 43/653* (2013.01); *A01N 43/68* (2013.01); *A01N 43/707* (2013.01); *A01N 43/713* (2013.01); *A01N 43/76* (2013.01); *A01N 43/80* (2013.01); *A01N 43/82* (2013.01); *A01N 43/90* (2013.01); *A01N 47/36* (2013.01)

(58) Field of Classification Search
CPC ........ A01N 57/20; A01N 43/54; A01N 43/76; A01N 33/18; A01N 37/34; A01N 43/653; A01N 37/10; A01N 43/90; A01N 43/713; A01N 43/10; A01N 43/40; A01N 43/707; A01N 43/68; A01N 47/36; A01N 43/82; A01N 25/00
See application file for complete search history.

(56) References Cited

U.S. PATENT DOCUMENTS

| | | | |
|---|---|---|---|
| 4,902,340 A | 2/1990 | Hubele | |
| 6,251,827 B1 | 6/2001 | Ziemer et al. | |
| 6,914,035 B2 | 7/2005 | Ziemer et al. | |
| 8,404,618 B2 | 3/2013 | Plant et al. | |
| 8,481,749 B2 | 7/2013 | Braun et al. | |
| 8,551,918 B2 | 10/2013 | Polge | |
| 8,822,378 B2 | 9/2014 | Braun et al. | |
| 2012/0058892 A1* | 3/2012 | Braun .................. | A01N 43/653 504/103 |

FOREIGN PATENT DOCUMENTS

| | | |
|---|---|---|
| CH | 2004/000767 | 4/2004 |
| EP | 11176378 | 8/2011 |
| WO | 98/47356 A2 | 10/1998 |
| WO | 02/060255 A2 | 8/2002 |
| WO | 03/022050 A1 | 3/2003 |
| WO | 2004/014138 A1 | 2/2004 |

(Continued)

OTHER PUBLICATIONS

International Search Report from corresponding PCT/EP2013/060468, dated Jul. 22, 2013.
Owen "Herbicidal Compositions", Declaration of Dr. Michael D.K. Owen, (Mar. 26, 2013), p. 1-71.
Owen "Professor and Weed Science Extension Specialist", Resume, p. 1-118.
Polge "Herbicidal Compositions", U.S. Appl. No. 60/527,061, filed Dec. 4, 2003, pp. 1-22.
Owen et al. "Evaluation of preemergence applications of KIH-485, s-metolachlor & CGA-154281, and s-metolachlor 3, atrazine & CGA-154281 for crop phytotoxicity and weed control in corn, Nashua, IA, 2003," (2003), NCWSS Research Report, vol. 60, pp. 51-52 (2003).

(Continued)

*Primary Examiner* — John Pak
*Assistant Examiner* — Andriae M Holt
(74) *Attorney, Agent, or Firm* — McBee Moore Woodward & Vanik IP, LLC

(57) ABSTRACT

Herbicidal compositions are described, comprising active compounds from the group of the N-(tetrazol-5-yl)- and N-(triazol-5-yl)arylcarboxamides and further herbicides and optionally safeners. These herbicidal compositions are particularly suitable for use against harmful plants in crops of useful plants.

8 Claims, No Drawings

(56) References Cited

FOREIGN PATENT DOCUMENTS

| WO | 2005/055716 A2 | 6/2005 |
|---|---|---|
| WO | 2005/104848 A1 | 11/2005 |
| WO | 2012028579 A1 | 3/2012 |
| WO | 2013017559 A1 | 2/2013 |

OTHER PUBLICATIONS

Joanna Davies "Herbicide Safeners—Commercial Products and Tools for Agrochemical Research", Pesticide Outlook, The Royal Society of Chemistry, (Feb. 2001) pp. 10-15.
Fedtke et al. "Synergistic Activity of the Herbicide Safener Dichlormid with Herbicides Affecting Photosynthesis", Zeitschrift für Naturforschung, Section C, Biosciences 1990 vol. 45 No. 5 pp. 565-556.
Sprague et al. "Enhancing the Margin of Selectivity of RPA 201772 in Zea mays with Antidotes", Weed Science, vol. 47, No. 5, pp. 492-497 (Sep.-Oct. 1999).
Leuschen et al. "Effects of a Seed-Applied Safener on Corn Injury From Clomazone, Imazaquin and Imazethapyr", University of Minnesota Southern Experiment Station Research Report, pp. 72-73 (1989).
Pyroxasulfone (KIH-485) chemical structure, Wildlife International, Ltd., pp. 1-7.
"Corn Injury from Balance Herbicide", University of Illinois Extension Publication (May 28, 1999), pp. 1-5.
"Herbicide Manual for Agricultural Professionals", Iowa State University Manual for Agricultural Professionals (2004).
Friesen et al. "The Influence of Temperature and Soil Moisture on the Phytotoxicity of Dicamba, Picloram, Bromoxynil, and 2,4-D Ester", Can. J. Plant Sci. (1966); vol. 46: pp. 653-660.
"Herbicide Injury Symptoms on Corn and Soybean", Purdue Extension Publication, printed (Apr. 13, 2017), pp. 1-7.
David W. Cudney "Why Herbicides are Selective", California Exotic Pest Plant Council (1996) Symposium Proceedings, pp. 1-3.
J.D. Burton et al. "Sulfonylurea Selectivity and Safener Activity in Landmark and 'Merit' Sweet Corn", Pesticide Biochem. and Physiol. (1994); vol. 48(3): pp. 163-172.
Maxwell et al. "Crop response from corn herbicides on two sweet corn varieties". Urbana, Illinois, (2004). NCWSS Research Report, vol. 61, pp. 8-10.
Gunsolus et al. "Herbicide Mode of Action and Injury Symptoms", North Central Regional Publication 377: (2002) pp. 1-19.
O'Sullivan et al. "Sweet corn (Zea mays) cultivar tolerance to primisulfuron", Can. J. Plant Sci. (2001); pp. 261-264.
Hwang et al. "Mode of Safening Action of Naphthalic Anhydride Against Injury of Sulfonylurea and Imidazolinone Herbicides in Maize", Council of the Australasian Weed Soc. Inc., 10th Australian Weeds Conference/14th Asian-Pacific Weed Science Society Conference 1993.
Rowe et al. I., Efficacy and Mode of Action of CGA-154281, A Protectant for Corn (Zea mays) from Metolachlor Injury. Weed Science. 1991; 39:78-82.
Zidua Herbicide Label from BASF, (2016).
Ritter et al., First Year Experiences with KIH-485. NEWSS 58:18 (2004) http://www.newss.org/proceedings_2004_vol58.pdf., pp. 1-5.
Zollinger et al. "Crop Response to KIH-485 carryover". NCWSS Research Report, vol. 61, pp. 34-35 (2004).
Mallory-Smith et al. "Revised Classification of Herbicides by Site of Action for Weed Resistance Management Strategies", Weed Technology. (2003); vol. 17: pp. 605-619.
Wicks et al. "Isoxaflutole (Balance) Herbicide Injury to Corn in Nebraska", pp. 1-8.
Jewell et al. "Preemergence weed control in corn with s-metolachlor &atrazine&mesotrione and s-metolachlor&mesotrion premixes. Wanatah, IN, 2003", (2003), NCWSS Research Report, vol. 60, pp. 70-71.
Nelson et al. "Safening of Isoxaflutole in Corn", NCWSS Research Report, vol. 56, p. 76 (2001).
Steckel et al. "Soil Factor Effects on Isoxaflutole Plus Flufenacet Phytotoxicity in Two Corn Hybrids". NCWSS Research Report, vol. 56, p. 145 (2001).
Kelley et al. "Soybean Response to Plant Growth Regulatory Herbicides", NCWSS Research Report, vol. 56, p. 100 (2001).
Ditmarsen et al. "Crop Tolerance and Efficacy of Flumetsulam + Clopyralid Tank Mixed With Reduced Rates of Dicamba + Diflufenzopyr in Field Corn", NCWSS Research Report, vol. 56, p. 218 (2001).
Wyk et al. "Maize Cultivars Differ in Tolerance to Imazethapyr", South African Journal of Plant and Soil (2000); 17:2, p. 86-89.
Curran et al. "Herbicide Injury—Photosynthetic Inhibitors and Contact Herbicides", University of Illinois Extension.
Phatak et al. "Chapter 13: Growth Regulators, Fungicides and other Agrochemicals as Herbicide Safeners", Crop Safeners for Herbicides (1989) pp. 299-315.
Owen et al. "Evaluation of Crop Phytotoxicity and Weed Control in Corn With Postemergence Applied Nicosulfuron & Rimsulfuron, Atrazine, Mesotrione and others, Ames, IA, 2002," (2002), NCWSS Research Report, vol. 59, p. 108-109.
Trower "Sweet Corn Tolerance to Postemergence Applications of Formasulfuron" (2003) NCWSS Research Report, vol. 60, pp. 16-17.
Johnson et al. "Nicosulfuron, Primisulfuron, Imazethapyr and DPX-PE350 Injury to Succeeding Crops" (1993), Weed Tech.; vol. 7(3): 641-644.
Striegel et al. "Formasulfuron + Isoxadifen—Success and Lessons Learned from a Launch Year", North Central Weed Science Proceedings, vol. 57: 225 (2002).
DuPont Web Printout explaining "Q" herbicides, "Safened Sulfonylurea Herbicides Reduce Risk of Corn Injury", Pioneer, printed (Apr. 14, 2007) pp. 1-6.
Schultz et al. "A Comparison of Safeners for Metolachlor on Corn", North Central Weed Science Proceedings, vol. 59:11 (2004), pp. 1-2.
Rowe et al. "Factors Affecting Chloroacetanilide Injury to Corn" (Zea mays). Weed Technology. 1990; 4(4): 904-906.
"Postemergence Control of Grass Weeds in field Corn" Purdue Weed Science, Publication (May 21, 2003), pp. 1-3.
David Hest "Mixing It Up", Farm Industry News (Jan. 1, 2003), pp. 1-10.
Hartzler et al. "2005 Iowa State University Manual for Agricultural Professionals" (1996-2006) pp. 1-115.
"Isoxaflutole" chemical structure, Phenomenex Applications; printed (Apr. 26, 2017). pp. 1-2.

\* cited by examiner

HERBICIDAL COMPOSITIONS COMPRISING N-TETRAZOL-5-YL)- OR N-(TRIAZOL-5-YL)ARYLCARBOXAMIDES

CROSS REFERENCE TO RELATED APPLICATIONS

This application is a §371 National Stage Application of PCT/EP2013/060468, filed May 22, 2013, which claims priority to EP 12169189.3, filed May 24, 2012.

BACKGROUND

Field of the Invention

The present invention relates to agrochemically active herbicidal compositions, to processes for production thereof and to the use thereof for control of harmful plants.

Description of Related Art

WO 2012028579 A1 and the non-prior-published EP11176378 with earlier priority disclose certain N-(tetrazol-5-yl)- and N-(triazol-5-yl)arylcarboxamides having herbicidal properties. However, these active compounds are not always sufficiently active against harmful plants and/or some of them are not fully compatible with some important crop plants such as cereal species, corn or rice.

Accordingly, it is an object of the present invention to provide herbicidal compositions in which the activity against harmful plants and/or selectivity of the abovementioned herbicides with respect to important crop plants is increased. This object is achieved by the herbicidal compositions according to the invention which are described below and comprise certain N-(tetrazol-5-yl)- and N-(triazol-5-yl) arylcarboxamides, further herbicides and optionally safeners.

SUMMARY

The present invention provides herbicidal compositions comprising
(A) one or more compounds of the formula (I) (component A) or salts thereof

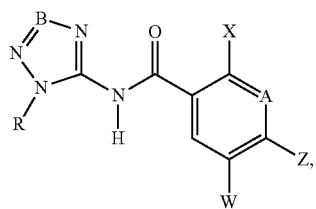

(I)

in which the symbols and indices are each defined as follows:
A represents N or CY,
B represents N or CH,
X represents nitro, halogen, cyano, formyl, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $NR_1R_2$, $P(O)(OR^5)_2$, $CH_2P(O)(OR^5)_2$, $(C_1-C_6)$-alkylheteroaryl, $(C_1-C_6)$-alkylheterocyclyl, where the two last-mentioned radicals are each substituted by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups, Y represents hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $CO(NOR^1)R^1$, $NR^1SO_2R^2$, $NR^1COR^1$, $OR^1$, $OSO_2R^2$, $S(O)_nR^2$, $SO_2OR^1$, $SO_2N(R^1)_2$ $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$CN$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, $CH_2P(O)(OR^5)_2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the six last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z represents halogen, cyano, thiocyanato, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $OCOOR^1$, $NR^1COOR^1$, $C(O)N(R^1)_2$, $NR^1C(O)N(R^1)_2$, $OC(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $N(R^1)_2$, $P(O)(OR^5)_2$, heteroaryl, heterocyclyl or phenyl, where the three last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy or halo-$(C_1-C_6)$-alkoxy, and where heterocyclyl carries n oxo groups, or Z may also represent hydrogen, $(C_1-C_6)$-alkyl or $(C_1-C_6)$-alkoxy if Y represents the $S(O)_nR^2$ radical, W represents hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_7)$-cycloalkyl, $(C_3-C_7)$-halocycloalkyl, $(C_1-C_6)$-alkoxy, $(C_1-C_6)$-haloalkoxy, $S(O)_n$—$(C_1-C_6)$-alkyl, $S(O)_n$—$(C_1-C_6)$-haloalkyl, $(C_1-C_6)$-alkoxy-$(C_1-C_4)$-alkyl, $(C_1-C_6)$-alkoxy-$(C_1-C_4)$-haloalkyl, halogen, nitro, $NR^3COR^3$ or cyano, R represents $(C_1-C_8)$-alkyl, halo-$(C_1-C_8)$-alkyl, $(C_2-C_8)$-alkenyl, halo-$(C_2-C_8)$-alkenyl, $(C_2-C_8)$-alkynyl, halo-$(C_2-C_8)$-alkynyl, where these six abovementioned radicals are each substituted by s radicals from the group consisting of hydroxyl, nitro, cyano, $SiR^5_3$, $PO(OR^5)_2$, $S(O)_n$—$(C_1-C_6)$-alkyl, $S(O)_n$—$(C_1-C_6)$-haloalkyl, $(C_1-C_6)$-alkoxy, halo-$(C_1-$ $C_6$)-alkoxy, $N(R^3)_2$, $COR^3$, $COOR^3$, $OCOR^3$, $NR^3COR^3$, $NR^3SO_2R^4$, $O(C_1$-$C_2)$-alkyl-$(C_3$-$C_6)$-cycloalkyl, $(C_3$-$C_6)$-cycloalkyl, heteroaryl, heterocyclyl, phenyl, Q-heteroaryl, Q-heterocyclyl, Q-phenyl and Q-benzyl, where the seven last-mentioned radicals are each substituted by s radicals from the group consisting of methyl, ethyl, methoxy, trifluoromethyl, cyano and halogen, and where heterocyclyl carries n oxo groups, or R represents $(C_3$-$C_7)$-cycloalkyl, heteroaryl, heterocyclyl or phenyl, each substituted by s radicals from the group consisting of halogen, nitro, cyano, $(C_1$-$C_6)$-alkyl, halo-$(C_1$-$C_6)$-alkyl, $(C_3$-$C_6)$-cycloalkyl, $S(O)_n$—$(C_1$-$C_6)$-alkyl, $(C_1$-$C_6)$-alkoxy, halo-$(C_1$-$C_6)$-alkoxy and $(C_1$-$C_6)$-alkoxy-$(C_1$-$C_4)$-alkyl, where heterocyclyl carries n oxo groups, Q represents O, S or $NR^3$, $R^1$ represents hydrogen, $(C_1$-$C_6)$-alkyl, $(C_1$-$C_6)$-haloalkyl, $(C_2$-$C_6)$-alkenyl, $(C_2$-$C_6)$-haloalkenyl, $(C_2$-$C_6)$-alkynyl, $(C_2$-$C_6)$-haloalkynyl, $(C_3$-$C_6)$-cycloalkyl, $(C_3$-$C_6)$-cycloalkenyl, $(C_3$-$C_6)$-halocycloalkyl, $(C_1$-$C_6)$-alkyl-O—$(C_1$-$C_6)$-alkyl, $(C_3$-$C_6)$-cycloalkyl-$(C_1$-$C_6)$-alkyl, phenyl, phenyl-$(C_1$-$C_6)$-alkyl, heteroaryl, $(C_1$-$C_6)$-alkylheteroaryl, heterocycl, $(C_1$-$C_6)$-alkylheterocyclyl, $(C_1$-$C_6)$-alkyl-O-heteroaryl, $(C_1$-$C_6)$-alkyl-O-heterocyclyl, $(C_1$-$C_6)$-alkyl-$NR^3$-heteroaryl or $(C_1$-$C_6)$-alkyl-$NR^3$-heterocyclyl, where the 21 last-mentioned radicals are each substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1$-$C_4)$-alkoxy-$(C_2$-$C_6)$-alkoxycarbonyl, and where heterocyclyl carries n oxo groups, $R^2$ represents $(C_1$-$C_6)$-alkyl, $(C_1$-$C_6)$-haloalkyl, $(C_2$-$C_6)$-alkenyl, $(C_2$-$C_6)$-haloalkenyl, $(C_2$-$C_6)$-alkynyl, $(C_2$-$C_6)$-haloalkynyl, $(C_3$-$C_6)$-cycloalkyl, $(C_3$-$C_6)$-cycloalkenyl, $(C_3$-$C_6)$-halocycloalkyl, $(C_1$-$C_6)$-alkyl-O—$(C_1$-$C_6)$-alkyl, $(C_3$-$C_6)$-cycloalkyl-$(C_1$-$C_6)$-alkyl, phenyl, phenyl-$(C_1$-$C_6)$-alkyl, heteroaryl, $(C_1$-$C_6)$-alkylheteroaryl, heterocyclyl, $(C_1$-$C_6)$-alkylheterocyclyl, $(C_1$-$C_6)$-alkyl-O-heteroaryl, $(C_1$-$C_6)$-alkyl-O-heterocyclyl, $(C_1$-$C_6)$-alkyl-$NR^3$-heteroaryl or $(C_1$-$C_6)$-alkyl-$NR^3$-heterocyclyl, where the 21 last-mentioned radicals are each substituted by s radicals from the group consisting of cyano, halogen, nitro, thiocyanato, $OR^3$, $S(O)_nR^4$, $N(R^3)_2$, $NR^3OR^3$, $COR^3$, $OCOR^3$, $SCOR^4$, $NR^3COR^3$, $NR^3SO_2R^4$, $CO_2R^3$, $COSR^4$, $CON(R^3)_2$ and $(C_1$-$C_4)$-alkoxy-$(C_2$-$C_6)$-alkoxycarbonyl, and where heterocyclyl carries n oxo groups, $R^3$ represents hydrogen, $(C_1$-$C_6)$-alkyl, $(C_2$-$C_6)$-alkenyl, $(C_2$-$C_6)$-alkynyl, $(C_3$-$C_6)$-cycloalkyl, $(C_3$-$C_6)$-cycloalkyl-$(C_1$-$C_6)$-alkyl or phenyl, $R^4$ represents $(C_1$-$C_6)$-alkyl, $(C_2$-$C_6)$-alkenyl, $(C_2$-$C_6)$-alkynyl, $(C_3$-$C_6)$-cycloalkyl, $(C_3$-$C_6)$-cycloalkyl-$(C_1$-$C_6)$-alkyl or phenyl, $R^5$ represents $(C_1$-$C_4)$-alkyl, n represents 0, 1 or 2, s represents 0, 1, 2 or 3, and (B) one or more herbicides (component B) selected from groups B1 to B11:

B1 1,3-diketo compounds, comprising prohexadione-calcium, trinexapac-ethyl, alloxydim, clethodim, cycloxydim, profoxydim, sethoxydim, tepraloxydim, tralkoxydim, mesotrione, sulcotrione, tefuryltrione, tembotrione, bicyclopyrone, pinoxaden, B2 (sulfon)amides, comprising beflubutamide, bromobutide, dimethenamide, dimethenamide-P, diphenamide, napropamide, pethoxamid, N-[3-chloro-4-(1-methylethyl)-phenyl]-2-methylpentanamide, naptalam, propyzamide, diflufenican, etobenzanid, flufenacet, mefenacet, mefluidide, pentanochlor, picolinafen, propanil, N-phenylphthalamic acid, acetochlor, alachlor, butachlor, dimethachlor, metazachlor, metolachlor, S-metolachlor, pretilachlor, propachlor, propisochlor, (2-chloro-6'-ethyl-N-isopropoxymethylaceto-o-toluidide), thenylchlor, asulam, carbaryl, carbetamide, chlorpropham, desmedipham, phenmedipham, propham, butylate, cycloate, dimepiperate, EPTC, esprocarb, methasulfocarb, molinate, orbencarb, pebulate, prosulfocarb, pyributicarb, thiobencarb, tri-allate, vernolate, amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucetosulfuron, flupyrsulfuron-methyl-sodium, foramsulfuron, halosulfuron-methyl, imazosulfuron, iodosulfuron-methyl-sodium, mesosulfuron-methyl, metsulfuron-methyl, monosulfuron, nicosulfuron, orthosulfamuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron (sodium), triflusulfuron-methyl, tritosulfuron, (benzoic acid, 2-[[[[(4-methoxy-6-(methylthio)-2-pyrimidinyl]amino]carbonyl]amino]sulfonyl]methyl ester), flucarbazone-sodium, propoxycarbazone-sodium, thiencarbazone-methyl, cloransulam-methyl, diclosulam, florasulam, flumetsulam, metosulam, penoxsulam, pyroxsulam, B3 arylnitriles, comprising bromoxynil, dichlobenil, ioxynil, pyraclonil, B4 azoles, comprising benzofenap, pyrazolynate, pyrazoxyfen, pyroxasulfone, topramezone, pyrasulfotole, 3-(3-chloro-5-{[1-methyl-3-(trifluoromethyl)-1H-pyrazol-5-yl]oxy}phenoxy)-1-methyl-5-(trifluoromethyl)-1H-pyrazole, 3-(3-iodo-5-{[1-methyl-3-(trifluoromethyl)-1H-pyrazol-5-yl]oxy}phenoxy)-1-methyl-5-(trifluoromethyl)-1H-pyrazole, 1-ethyl-3-(3-fluoro-5-{[1-methyl-3-(trifluoromethyl)-1H-pyrazol-5-yl]oxy}phenoxy)-5-(trifluoromethyl)-1H-pyrazole, pyraflufen-ethyl, fluazolate, isouron, isoxaben, isoxaflutole, imazamethabenzmethyl, imazamox, imazapic, imazapyr, imazaquin, imazethapyr, methazole, oxadiargyl, oxadiazon, amicarbazone, carfentrazone-ethyl, sulfentrazone, bencarbazone, amitrole, paclobutrazol, uniconazole, cafenstrole, fentrazamide, B5 other herbicides, comprising aminocyclopyrachlor, N-acetylthiazolidine-4-carboxylic acid, acrolein, aminopyralid, ammonium pelargonate, ammonium sulfamate, aviglycine, benazolin, benfluralin, benfuresate, bentazone, benzobicyclon, 6-benzylaminopurine, borax, butralin, carvone, catechin, chlorflurenol-methyl, chloridazon, chlormequat chloride, chloroacetic acid, chlorphthalim, chlorthal-dimethyl, cinidon-ethyl, cinmethylin, clofencet, clomazone, cloxyfonac, cyanamide, cyclanilide, 6-isopentylaminopurin, kinetin, zeatin, dalapon, daminozide, dazomet, n-decanol, difenzoquat metilsulfate, 2,6-diisopropylnaphthalene, dikegulac, dimethipin, dimethylarsenic acid, dinitramine, dinoterb, diquat dibromide, dithiopyr, DNOC, endothal, ethafluralin, ethofumesate, ethylchlozate, ferrous sulfate, flamprop-M-methyl, flufenpyr-ethyl, flumetralin, flumiclorac-pentyl, flumioxazin, flupropanate, flurenol, fluridone, flurochloridone, flurtamone, gibberillic acid, indanofan, isopropalin, isoprothiolane, maleic hydrazide, mepiquat chloride, metam, methylarsonic acid, 1-methylcyclopropene, methyl isothiocyanate, nitrophenolate mixture, nonanoic acid, norflurazon, oleic acid, oryzalin, oxaziclomefone, paraquat dichloride, pendimethalin, pentachlorophenol, pentoxazone, petroleum oils, prodiamine, n-propyl dihydrojasmonate, pyridate, quinoclamine, sintofen, sodium chlorate, sulfuric acid, tar oils, TCA sodium, tecnazene, thiazopyr, triacontanol, trifluralin and urea sulfate, B6 (het)arylcarboxylic acids, comprising dicamba, 2,3,6-TBA, clopyralid, fluroxypyr, inabenfide, picloram, triclopyr, quinclorac, quinmerac, indol-3-ylacetic acid, 4-indol-3-yl-butyric acid, 2-(1-naphthyl)acetamide, 1-naphthylacetic acid, 2-naphthyloxyacetic acid, B7 organic phosphorus compounds, comprising anilofos, bensulide, bilanafos, butimafos, fosamine, glufosinate, glufosinate salts, glufosinate-ammonium, glufosinate-sodium, L-glufosinate-ammonium, L-glufosinate-sodium, glyphosate, glyphosate-isopropyl-ammonium, glyphosate-ammonium, glyphosate-trimesium (=sulfosate), glyphosate-diammonium, glyphosate-potassium, piperophos, ethephon and tribufos, B8 phenyl ether, comprising acifluorfen-sodium, aclonifen, fluoroglycofen-ethyl, fomesafen, lactofen, oxyfluorfen, bifenox, ethoxyfen-ethyl, clomeprop, cloprop, dichlorprop, dichlorprop-P, mecoprop, mecoprop-P, 4-CPA, 2,4-D, MCPA, MCPA-thioethyl, 2,4-DB, MCPB, clodinafop-propargyl, cyhalofop-butyl, diclofop-methyl, diclofop-P-methyl, fenoxaprop-P-ethyl, fluazifop-butyl, fluazifop-P-butyl, haloxyfop, haloxyfop-P, metamifop, propaquizafop, quizalafop, quizalafop-P, B9 pyrimidines, comprising ancymidol, flurprimidol, pyrimisulfan, bispyribac-sodium, pyribenzoxim, pyriminobac-methyl, pyribambenz-isopropyl, pyribambenz-propyl, pyriftalid, pyrithiobac-sodium, benzfendizone, bromacil, butafenacil, lenacil, terbacil, 2-chloro-4-fluoro-5-[3-methyl-2,6-dioxo-4-(trifluoromethyl)-3,6-dihydropyrimidin-1(2H)-yl]-N-[methyl(1-methylethyl)-sulfamoyl]benzamide, B10 (thio)ureas, comprising cumyluron, chlorbromuron, chlorotoluron, chloroxuron, daimuron, diflufenzopyr, dimefuron, diuron, fluometuron, forchlorfenuron, isoproturon, karbutilate, linuron, methyldymron, metobromuron, metoxuron, monolinuron, neburon, siduron, thidiazuron, methiuron, tebuthiuron, methabenzthiazuron, B11 triazines, comprising triaziflam, indaziflam, atrazine, cyanazine, propazine, simazine, terbuthylazine, trietazine, prometon, ametryn, dimethametryn, prometryn, simetryn, terbutryn, hexazinon, metamitron, metribuzin.

DETAILED DESCRIPTION OF A PREFERRED EMBODIMENT

In a further embodiment, these herbicidal compositions comprise C) one or more safeners (component C) from the group consisting of benoxacor (C1), cloquintocet-mexyl (C2), cyprosulfamide (C3), dichlormid (C4), fenclorim (C5), fenchlorazole (C6), furilazole (C7), isoxadifen-ethyl (C8), mefenpyr-diethyl (C9), 4-(dichloroacetyl)-1-oxa-4-azaspiro[4.5]decane of CAS 71526-07-3 (C10), 2,2,5-trimethyl-3-(dechloroacetyl)-1,3-oxazolidine of CAS 52836-31-4 (C11).

Components B) and C) are known, for example, from "The Pesticide Manual", 15th edition, The British Crop Protection Council and the Royal Soc. of Chemistry, and from the website http://www.alanwood.net/pesticides/.

The inventive herbicidal compositions may comprise or be used together with additional further components, for example other kinds of active crop protection ingredients and/or additives and/or formulation auxiliaries customary in crop protection.

The herbicides (A), (B) and optionally the safeners (C) can be applied in a known manner, for example together (for example as a co-formulation or as a tank-mix) or else at different times in short succession (splitting), for example to the plants, plant parts, plant seeds or the area on which the plants grow. It is possible, for example, to apply the individual active compounds or the herbicide-safener combination in several portions (sequential application), for example pre-emergence applications followed by post-emergence applications, or early post-emergence applications followed by post-emergence applications at an intermediate or late stage. Preference is given to the joint or immediately successive application of the active compounds in the respective combination. It is also possible to use the individual active compounds or the herbicide-safener combination for seed treatment.

Preference is given to those compositions according to the invention which comprise, as herbicide (A), those compounds of the general formula (I) and salts thereof in which A represents N or CY, B represents N or CH, X represents nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_1-C_6)$-alkyl-O—$(C_1-C_6)$-alkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $OCOR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$ or $(C_1-C_6)$-alkyl-$NR^1SO_2R^2$, $(C_1-C_6)$-alkylheteroaryl, $(C_1-C_6)$-alkylheterocyclyl, where the two last-mentioned radicals are each substituted by s radicals from the group consisting of halogen, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups, Y represents hydrogen, nitro, halogen, cyano, thiocyanato, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, $(C_3-C_6)$-cycloalkenyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $OR^1$, $COOR^1$, $OSO_2R^2$, $S(O)_nR^2$, $SO_2OR^1$, $SO_2N(R^1)_2$, $N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, $(C_1-C_6)$-alkylphenyl, $(C_1-C_6)$-alkylheteroaryl, $(C_1-C_6)$-alkylheterocyclyl, phenyl, heteroaryl or heterocyclyl, where the six last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy, $(C_1-C_6)$-alkoxy-$(C_1-C_4)$-alkyl and cyanomethyl, and where heterocyclyl carries n oxo groups, Z represents halogen, cyano, thiocyanato, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^1$, $COOR^1$, $C(O)N(R^1)_2$, $C(O)NR^1OR^1$, $OSO_2R^2$, $S(O)_nR^2$, $SO_2OR^1$, $SO_2N(R^1)_2$, $NR^1SO_2R^2$, $NR^1COR^1$, $(C_1-C_6)$-alkyl-$S(O)_nR^2$, $(C_1-C_6)$-alkyl-$OR^1$, $(C_1-C_6)$-alkyl-$OCOR^1$, $(C_1-C_6)$-alkyl-$OSO_2R^2$, $(C_1-C_6)$-alkyl-$CO_2R^1$, $(C_1-C_6)$-alkyl-$SO_2OR^1$, $(C_1-C_6)$-alkyl-$CON(R^1)_2$, $(C_1-C_6)$-alkyl-$SO_2N(R^1)_2$, $(C_1-C_6)$-alkyl-$NR^1COR^1$, $(C_1-C_6)$-alkyl-$NR^1SO_2R^2$, 1,2,4-triazol-1-yl, or Z may also represent hydrogen, $(C_1-C_6)$-alkyl or $(C_1-C_6)$-alkoxy if Y represents the $S(O)_nR^2$ radical, W represents hydrogen, $(C_1-C_6)$-alkyl, halo-$(C_1-C_6)$-alkyl, $(C_1-C_6)$-alkoxy, $(C_1-C_6)$-haloalkoxy, $S(O)_n$—$(C_1-$ $C_6$)-alkyl, S(O)$_n$—($C_1$-$C_6$)-haloalkyl, ($C_1$-$C_6$)-alkoxy-($C_1$-$C_4$)-alkyl, halogen, nitro or cyano, R represents ($C_1$-$C_8$)-alkyl, halo-($C_1$-$C_8$)-alkyl, ($C_2$-$C_8$)-alkenyl, halo-($C_2$-$C_8$)-alkenyl, ($C_2$-$C_8$)-alkynyl, halo-($C_2$-$C_8$)-alkynyl, where these six abovementioned radicals are each substituted by s radicals from the group consisting of nitro, cyano, SiR$^5_3$, P(OR$^5$)$_3$, S(O)$_n$—($C_1$-$C_6$)-alkyl, ($C_1$-$C_6$)-alkoxy, halo-($C_1$-$C_6$)-alkoxy, N(R$^3$)$_2$, COR$^3$, COOR$^3$, OCOR$^3$, NR$^3$COR$^3$, NR$^3$SO$_2$R$^4$, ($C_3$-$C_6$)-cycloalkyl, heteroaryl, heterocyclyl, phenyl, Q-heteroaryl, Q-heterocyclyl, Q-phenyl and Q-benzyl, where the seven last-mentioned radicals are each substituted by s radicals from the group consisting of methyl, ethyl, methoxy, trifluoromethyl, cyano and halogen, and where heterocyclyl carries n oxo groups, or R represents ($C_3$-$C_7$)-cycloalkyl, heteroaryl, heterocyclyl or phenyl, each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$—($C_1$-$C_6$)-alkyl, ($C_1$-$C_6$)-alkoxy, halo-($C_1$-$C_6$)-alkoxy and ($C_1$-$C_6$)-alkoxy-($C_1$-$C_4$)-alkyl, Q represents O, S, or NR$^3$, R$^1$ represents hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-NR$^3$-heteroaryl or ($C_1$-$C_6$)-alkyl-NR$^3$-heterocyclyl, where the sixteen last-mentioned radicals are each substituted by s radicals from the group consisting of cyano, halogen, nitro, OR$^3$, S(O)$_n$R$^4$, N(R$^3$)$_2$, NR$^3$OR$^3$, COR$^3$, OCOR$^3$, NR$^3$COR$^3$, NR$^3$SO$_2$R$^4$, CO$_2$R$^3$, CON(R$^3$)$_2$ and ($C_1$-$C_4$)-alkoxy-($C_2$-$C_6$)-alkoxycarbonyl, and where heterocyclyl carries n oxo groups, R$^2$ represents ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-NR$^3$-heteroaryl or ($C_1$-$C_6$)-alkyl-NR$^3$-heterocyclyl, where these sixteen last-mentioned radicals are each substituted by s radicals from the group consisting of cyano, halogen, nitro, OR$^3$, S(O)$_n$R$^4$, N(R$^3$)$_2$, NR$^3$OR$^3$, NR$^3$SO$_2$R$^4$, COR$^3$, OCOR$^3$, NR$^3$COR$^3$, CO$_2$R$^3$, CON(R$^3$)$_2$ and ($C_1$-$C_4$)-alkoxy-($C_2$-$C_6$)-alkoxycarbonyl, and where heterocyclyl carries n oxo groups, R$^3$ represents hydrogen, ($C_1$-$C_6$)-alkyl, ($C_2$-$C_6$)-alkenyl, ($C_2$-$C_6$)-alkynyl, ($C_3$-$C_6$)-cycloalkyl or ($C_3$-$C_6$)-cycloalkyl-($C_1$-$C_6$)-alkyl, R$^4$ represents ($C_1$-$C_6$)-alkyl, ($C_2$-$C_6$)-alkenyl or ($C_2$-$C_6$)-alkynyl, R$^5$ represents methyl or ethyl, n represents 0, 1 or 2, and s represents 0, 1, 2 or 3.

Preference is also given to compositions according to the invention which comprise, as herbicide (A), those compounds of the general formula (I) and salts thereof in which A represents N or CY, B represents N or CH, X represents nitro, halogen, cyano, ($C_1$-$C_6$)-alkyl, halo-($C_1$-$C_6$)-alkyl, ($C_3$-$C_6$)-cycloalkyl, OR$^1$, S(O)$_n$R$^2$, ($C_1$-$C_6$)-alkyl-S(O)$_n$R$^2$, ($C_1$-$C_6$)-alkyl-OR$^1$, ($C_1$-$C_6$)-alkyl-CON(R$^1$)$_2$, ($C_1$-$C_6$)-alkyl-SO$_2$N(R$^1$)$_2$, ($C_1$-$C_6$)-alkyl-NR$^1$COR$^1$, ($C_1$-$C_6$)-alkyl-NR$^1$SO$_2$R$^2$, ($C_1$-$C_6$)-alkylheteroaryl, ($C_1$-$C_6$)-alkylheterocyclyl, where the two last-mentioned radicals are each substituted by s halogen, ($C_1$-$C_6$)-alkyl, halo-($C_1$-$C_6$)-alkyl, S(O)$_n$—($C_1$-$C_6$)-alkyl, ($C_1$-$C_6$)-alkoxy and halo-($C_1$-$C_6$)-alkoxy radicals, and where heterocyclyl carries n oxo groups, Y hydrogen, nitro, halogen, cyano, ($C_1$-$C_6$)-alkyl, ($C_1$-$C_6$)-haloalkyl, OR$^1$, S(O)$_n$R$^2$, SO$_2$N(R$^1$)$_2$, N(R$^1$)$_2$, NR$^1$SO$_2$R$^2$, NR$^1$COR$^1$, ($C_1$-$C_6$)-alkyl-S(O)$_n$R$^2$, ($C_1$-$C_6$)-alkyl-OR$^1$, ($C_1$-$C_6$)-alkyl-CON(R$^1$)$_2$, ($C_1$-$C_6$)-alkyl-SO$_2$N(R$^1$)$_2$, ($C_1$-$C_6$)-alkyl-NR$^1$COR$^1$, ($C_1$-$C_6$)-alkyl-NR$^1$SO$_2$R$^2$, ($C_1$-$C_6$)-alkylphenyl, ($C_1$-$C_6$)-alkylheteroaryl, ($C_1$-$C_6$)-alkylheterocyclyl, phenyl, heteroaryl or heterocyclyl, where the six last-mentioned radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$—($C_1$-$C_6$)-alkyl, ($C_1$-$C_6$)-alkoxy, halo-($C_1$-$C_6$)-alkoxy, ($C_1$-$C_6$)-alkoxy-($C_1$-$C_4$)-alkyl and cyanomethyl, and where heterocyclyl carries n oxo groups, Z represents halogen, cyano, halo-($C_1$-$C_6$)-alkyl, ($C_3$-$C_6$)-cycloalkyl, S(O)$_n$R$^2$, 1,2,4-triazol-1-yl, or Z may also represent hydrogen, methyl, methoxy or ethoxy if Y represents the S(O)$_n$R$^2$ radical, W represents hydrogen, methyl, ethyl, methoxymethyl, methoxy, fluorine, chlorine or S(O)$_n$CH$_3$, R represents ($C_1$-$C_8$)-alkyl, halo-($C_1$-$C_8$)-alkyl, ($C_2$-$C_8$)-alkenyl, halo-($C_2$-$C_8$)-alkenyl, ($C_2$-$C_8$)-alkynyl, halo-($C_2$-$C_8$)-alkynyl, where these six aforementioned radicals are each substituted by s radicals from the group consisting of cyano, S(O)$_n$—($C_1$-$C_6$)-alkyl, ($C_1$-$C_6$)-alkoxy, halo-($C_1$-$C_6$)-alkoxy, COR$^3$, COOR$^3$, OCOR$^3$, NR$^3$COR$^3$, NR$^3$SO$_2$R$^4$, ($C_3$-$C_6$)-cycloalkyl, heteroaryl, heterocyclyl and phenyl, where the three last-mentioned radicals are each substituted by s radicals from the group consisting of methyl, ethyl, methoxy, trifluoromethyl, cyano and halogen, and where heterocyclyl carries 0 to 2 oxo groups, or R represents phenyl substituted by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$—($C_1$-$C_6$)-alkyl, ($C_1$-$C_6$)-alkoxy, halo-($C_1$-$C_6$)-alkoxy, ($C_1$-$C_6$)-alkoxy-($C_1$-$C_4$)-alkyl, R$^1$ represents hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, ($C_1$-$C_6$)-alkyl-O—($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-NR$^3$-heteroaryl or ($C_1$-$C_6$)-alkyl-NR$^3$-heterocyclyl, where the sixteen last-mentioned radicals are each substituted by s radicals from the group consisting of cyano, halogen, nitro, OR$^3$, S(O)$_n$R$^4$, N(R$^3$)$_2$, NR$^3$OR$^3$, COR$^3$, OCOR$^3$, NR$^3$COR$^3$, NR$^3$SO$_2$R$^4$, CO$_2$R$^3$, CON(R$^3$)$_2$ and ($C_1$-$C_4$)-alkoxy-($C_2$-$C_6$)-alkoxycarbonyl, and where heterocyclyl carries n oxo groups, R$^2$ represents ($C_1$-$C_6$)-alkyl, ($C_3$-$C_6$)-cycloalkyl or ($C_3$-$C_6$)-cycloalkyl-($C_1$-$C_6$)-alkyl, each substituted by s radicals from the group consisting of halogen and OR$^3$, R$^3$ represents hydrogen or ($C_1$-$C_6$)-alkyl, R$^4$ represents ($C_1$-$C_6$)-alkyl, R$^5$ represents methyl or ethyl, n represents 0, 1 or 2, and s represents 0, 1, 2 or 3.

Particular preference is given to those compositions according to the invention which comprise, as herbicide (A), compounds of the general formula (I) and salts thereof in which A represents CY, B represents N, X represents chlorine, methyl, ethyl, propyl, cyclopropyl, methoxy or $SO_2CH_3$, Y represents hydrogen, $CH_2OCH_3$, $CH_2OCH_2CF_3$, $CH_2OC_2H_4OCH_3$, 4,5-dihydro-1,2-oxazol-3-yl, 5-methoxymethy-4,5-dihydro-1,2-oxazol-3-yl, pyrazol-1-yl, OMe, OEt, OPr, OiBu, $OCH_2cPr$, $OC_2H_4OCH_3$, $SO_2CH_3$, $S(O)CH_3$ or $SCH_3$, $SO_2Et$, $S(O)Et$ or SEt, Z represents trifluoromethyl, $SO_2CH_3$, $SO_2Et$, chlorine or bromine, W represents hydrogen, and R represents methyl, ethyl, propyl or methoxyethyl.

Very particular preference is given to compositions according to the invention which comprise, as herbicide (A), those compounds of the general formula (I) and salts thereof in which A represents CY, B represents N, X represents chlorine, Y $SO_2CH_3$, $SOCH_3$ or $SO_2Et$, Z represents hydrogen or methyl, W represents hydrogen, and R represents methyl.

Very particular preference is also given to compositions according to the invention which comprise, as herbicide (A), those compounds of the general formula (I) and salts thereof in which A represents CY, B represents N X represents chlorine or bromine, Y represents hydrogen, methyl, $SO_2CH_3$ or $SCH_3$, Z represents hydrogen, $SO_2CH_3$ or $SCH_3$, W represents methyl, and R represents methyl or ethyl.

Very particular preference is also given to those compositions according to the invention which comprise, as herbicide (A), compounds of the general formula (I) and salts thereof in which A represents CY, B represents CH, X represents chlorine or methyl, Y represents 4,5-dihydro-1,2-oxazol-3-yl, pyrazol-1-yl, $OC_2H_4OCH_3$ or $SO_2CH_3$, Z represents trifluoromethyl, $SO_2CH_3$, $SO_2Et$ or chlorine, W represents hydrogen, and R represents methyl.

Very particular preference is also given to compositions according to the invention which comprise, as herbicide (A), those compounds of the general formula (I) and salts thereof in which A represents N, B represents N, X represents chlorine, bromine, $SO_2CH_3$, methoxymethyl, $OCH_2cPr$, $OC_2H_4OCH_3$ or methyl, Z represents trifluoromethyl, W represents hydrogen, and R represents methyl or ethyl.

In the formula (I) and all the formulae which follow, alkyl radicals having more than two carbon atoms may be straight-chain or branched. Alkyl radicals are, for example, methyl, ethyl, n- or isopropyl, n-, iso-, tert- or 2-butyl, pentyls, hexyls such as n-hexyl, isohexyl and 1,3-dimethylbutyl. Analogously, alkenyl represents, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl represents, for example, propargyl, but-2-yn-1-yl, but-3-yn-1-yl, 1-methylbut-3-yn-1-yl. The multiple bond may be in each case in any position of the unsaturated radical. Cycloalkyl represents a carbocyclic saturated ring system having three to six carbon atoms, for example cyclopropyl, cyclobutyl, cyclopentyl or cyclohexyl. Analogously, cycloalkenyl represents a monocyclic alkenyl group having three to six carbon ring members, for example cyclopropenyl, cyclobutenyl, cyclopentenyl and cyclohexenyl, where the double bond may be in any position.

Halogen represents fluorine, chlorine, bromine or iodine.

Heterocyclyl represents a saturated, semisaturated or fully unsaturated cyclic radical containing 3 to 6 ring atoms, of which 1 to 4 are from the group of oxygen, nitrogen and sulfur, and which may additionally be fused by a benzo ring. For example, heterocyclyl represents piperidinyl, pyrrolidinyl, tetrahydrofuranyl, dihydrofuranyl and oxetanyl.

Heteroaryl represents an aromatic cyclic radical containing 3 to 6 ring atoms, of which 1 to 4 are from the group of oxygen, nitrogen and sulfur, and which may additionally be fused by a benzo ring. Heteroaryl represents, for example, benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

When a group is polysubstituted by radicals, this means that this group is substituted by one or more identical or different radicals from those mentioned. This applies analogously to the formation of ring systems by various atoms and elements. At the same time, the scope of the claims shall exclude those compounds known to the person skilled in the art to be chemically unstable under standard conditions.

The present invention also provides herbicidal compositions comprising stereoisomers and mixtures thereof which are encompassed by formula (I) or by the formulae of component B. Such compounds of the formula (I) or of the formulae of component B contain, for example, one or more asymmetrically substituted carbon atoms or sulfoxides. The possible stereoisomers defined by the specific three-dimensional shape thereof, such as enantiomers and diastereomers, are all encompassed by the formula (I) or by components B and (C); especially also the racemic mixtures and where enantiomers are possible both enantiomers and especially the respective biologically active enantiomer. The individual stereoisomers can be obtained by customary methods from mixtures of the stereoisomers or else by stereoselective reactions in combination with the use of stereochemically pure starting materials or auxiliaries.

Examples of compounds used as herbicide (A) are listed in the following tables:

In these tables, the abbreviations used mean:

| | | | |
|---|---|---|---|
| Et = ethyl | Me = methyl | n-Pr = n-propyl | i-Pr = isopropyl |
| c-Pr = cyclopropyl | Ph = phenyl | Ac = acetyl | i-Bu = isobutyl |

TABLE 1

Compounds of the general formula (I) in which A represents CY and B represents N and W represents hydrogen

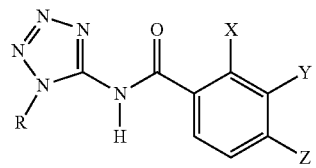

| Ex. No. | R | X | Y | Z |
|---|---|---|---|---|
| A1-1 | Me | Cl | H | SO$_2$Me |
| A1-2 | Me | SO$_2$Me | H | CF$_3$ |
| A1-3 | Me | Me | SMe | CF$_3$ |
| A1-4 | MeOC$_2$H$_4$ | Me | SMe | CF$_3$ |
| A1-5 | Me | Me | SOMe | CF$_3$ |
| A1-6 | Et | Me | SOMe | CF$_3$ |
| A1-7 | Me | Me | SO$_2$Me | CF$_3$ |
| A1-8 | Et | Me | SO$_2$Me | CF$_3$ |
| A1-9 | Pr | Me | SO$_2$Me | CF$_3$ |
| A1-10 | MeOC$_2$H$_4$ | Me | SO$_2$Me | CF$_3$ |
| A1-11 | Me | Me | SEt | CF$_3$ |
| A1-12 | Et | Me | SEt | CF$_3$ |
| A1-13 | Me | Me | SOEt | CF$_3$ |
| A1-14 | Et | Me | SOEt | CF$_3$ |
| A1-15 | Me | Me | SO$_2$Et | CF$_3$ |
| A1-16 | Et | Me | SO$_2$Et | CF$_3$ |
| A1-17 | Me | Me | SO$_2$Me | Cl |
| A1-18 | Me | Me | SEt | Cl |
| A1-19 | Me | Me | SOEt | Cl |
| A1-20 | Et | Me | SOEt | Cl |
| A1-21 | Me | Me | SO$_2$Et | Cl |
| A1-22 | Me | Me | SMe | Br |
| A1-23 | Me | Me | SEt | Br |
| A1-24 | Me | Me | 4,5-dihydro-1,2-oxazol-3-yl | SO$_2$Me |
| A1-25 | Et | Me | 4,5-dihydro-1,2-oxazol-3-yl | SO$_2$Me |
| A1-26 | Me | Me | pyrazol-1-yl | SO$_2$Me |
| A1-27 | Et | Me | pyrazol-1-yl | SO$_2$Me |
| A1-28 | Me | Me | SMe | SO$_2$Me |
| A1-29 | Me | Me | SO$_2$Me | SO$_2$Me |
| A1-30 | Et | Me | SO$_2$Me | SO$_2$Me |
| A1-31 | Me | Me | SO$_2$Et | SO$_2$Me |
| A1-32 | Et | Me | SO$_2$Et | SO$_2$Me |
| A1-33 | Me | Et | SMe | CF$_3$ |
| A1-34 | Me | Et | SOMe | CF$_3$ |
| A1-35 | Me | Et | SO$_2$Me | CF$_3$ |
| A1-36 | Me | Et | SMe | Cl |
| A1-37 | Et | Et | SMe | Cl |
| A1-38 | Me | Et | SOMe | Cl |
| A1-39 | Me | Et | SMe | Br |
| A1-40 | Me | Et | SO$_2$Me | Br |
| A1-41 | Me | Pr | SMe | CF$_3$ |
| A1-42 | Me | Pr | SOMe | CF$_3$ |
| A1-43 | Me | c-Pr | SMe | CF$_3$ |
| A1-44 | Me | OMe | SMe | CF$_3$ |
| A1-45 | Me | OMe | SOMe | CF$_3$ |
| A1-46 | Me | OMe | SO$_2$Me | CF$_3$ |
| A1-47 | Me | OMe | SEt | CF$_3$ |
| A1-48 | Me | Cl | SMe | H |
| A1-49 | Me | Cl | SO$_2$Me | Me |
| A1-50 | Me | Cl | SO$_2$Et | Me |
| A1-51 | Me | Cl | SO$_2$Me | CF$_3$ |
| A1-52 | Me | Cl | OC$_2$H$_4$OMe | Cl |
| A1-53 | Me | Cl | SMe | Cl |
| A1-54 | Et | Cl | SMe | Cl |
| A1-55 | Me | Cl | SOMe | Cl |
| A1-56 | Et | Cl | SOMe | Cl |
| A1-57 | Me | Cl | SO$_2$Me | Cl |
| A1-58 | Et | Cl | SO$_2$Me | Cl |
| A1-59 | Me | Cl | SO$_2$Et | Cl |
| A1-60 | Me | Cl | CH$_2$OMe | SO$_2$Me |
| A1-61 | Me | Cl | CH$_2$OCH$_2$CF$_3$ | SO$_2$Me |
| A1-62 | Et | Cl | CH$_2$OCH$_2$CF$_3$ | SO$_2$Me |
| A1-63 | Me | Cl | CH$_2$OC$_2$H$_4$OMe | SO$_2$Me |
| A1-64 | Me | Cl | 4,5-dihydro-1,2-oxazol-3-yl | SO$_2$Me |

TABLE 1-continued

Compounds of the general formula (I) in which A represents CY and B represents N and W represents hydrogen

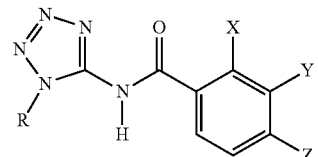

| Ex. No. | R | X | Y | Z |
|---|---|---|---|---|
| A1-65 | Me | Cl | 4,5-dihydro-1,2-oxazol-3-yl | SO$_2$Et |
| A1-66 | Me | Cl | 5-methoxymethy-4,5-dihydro-1,2-oxazol-3-yl | SO$_2$Et |
| A1-67 | Me | Cl | OMe | SO$_2$Me |
| A1-68 | Me | Cl | OMe | SO$_2$Et |
| A1-69 | Me | Cl | OEt | SO$_2$Me |
| A1-70 | Me | Cl | OEt | SO$_2$Et |
| A1-71 | Me | Cl | OPr | SO$_2$Me |
| A1-72 | Me | Cl | OPr | SO$_2$Et |
| A1-73 | Me | Cl | Oi-Bu | SO$_2$Me |
| A1-74 | Me | Cl | OCH$_2$c-Pr | SO$_2$Me |
| A1-75 | Me | Cl | OCH$_2$c-Pr | SO$_2$Et |
| A1-76 | Me | Cl | OC$_2$H$_4$OMe | SO$_2$Me |
| A1-77 | Me | Cl | SMe | SO$_2$Me |
| A1-78 | Me | Me | OMe | SO$_2$Me |
| A1-79 | Et | OMe | SMe | CHF$_2$ |
| A1-80 | Me | OMe | SO$_2$Me | CHF$_2$ |
| A1-81 | Me | OMe | SMe | CHF$_2$ |
| A1-82 | Me | OMe | SOMe | CHF$_2$ |
| A1-83 | Me | Cl | O(CH$_2$)$_3$OMe | SO$_2$Et |
| A1-84 | Et | Cl | SOMe | Me |
| A1-85 | Me | Cl | SMe | CF$_3$ |

TABLE 2

Compounds of the general formula (I) in which A represents CY and B represents CH and W represents hydrogen

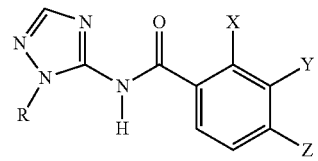

| Ex. No. | R | X | Y | Z |
|---|---|---|---|---|
| A2-1 | Me | Me | SO$_2$Me | CF$_3$ |
| A2-2 | Me | Me | 4,5-dihydro-1,2-oxazol-3-yl | SO$_2$Me |
| A2-3 | Me | Me | pyrazol-1-yl | SO$_2$Me |
| A2-4 | Me | Me | SO$_2$Me | SO$_2$Me |
| A2-5 | Me | Cl | SO$_2$Me | Cl |
| A2-6 | Me | Cl | 4,5-dihydro-1,2-oxazol-3-yl | SO$_2$Me |
| A2-7 | Me | Cl | 4,5-dihydro-1,2-oxazol-3-yl | SO$_2$Et |
| A2-8 | Me | Cl | OC$_2$H$_4$OMe | SO$_2$Me |
| A2-9 | Me | Cl | SO$_2$Me | CF$_3$ |
| A2-10 | Me | Cl | SO$_2$Et | CF$_3$ |

TABLE 3

Compounds of the general formula (I) in which A represents CY and B represents N

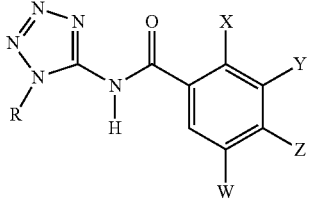

| Ex. No. | R  | X  | Y      | Z      | W  |
|---------|----|----|--------|--------|----|
| A3-1    | Me | Cl | H      | SMe    | Me |
| A3-2    | Me | Cl | SMe    | H      | Me |
| A3-3    | Me | Cl | SO$_2$Me | H    | Me |
| A3-4    | Et | Cl | SO$_2$Me | H    | Me |
| A3-5    | Me | Cl | Me     | SMe    | Me |
| A3-6    | Et | Cl | Me     | SO$_2$Me | Me |
| A3-7    | Me | Br | SO$_2$Me | H    | Me |

TABLE 4

Compounds of the general formula (I) in which A represents N and B represents N and W represents hydrogen

| Ex. No. | R  | X              | Z     |
|---------|----|----------------|-------|
| A4-1    | Me | Me             | CF$_3$ |
| A4-2    | Me | CH$_2$OMe      | CF$_3$ |
| A4-3    | Et | CH$_2$OMe      | CF$_3$ |
| A4-4    | Me | CH$_2$OC$_2$H$_4$OMe | CF$_3$ |
| A4-5    | Et | CH$_2$OC$_2$H$_4$OMe | CF$_3$ |
| A4-6    | Me | CH$_2$OCH$_2$c-Pr | CF$_3$ |
| A4-7    | Me | Cl             | CF$_3$ |
| A4-8    | Me | Br             | CF$_3$ |
| A4-9    | Me | SO$_2$Me       | CF$_3$ |

Preferred herbicides of group B1 are clethodim, sethoxydim, tepraloxydim, mesotrione, sulcotrione, tefuryltrione, tembotrione, bicyclopyrone, pinoxaden, tralkoxydim. Particularly preferred herbicides of group B1 are clethodim, sulcotrione, tefuryltrione, tembotrione, bicyclopyrone, pinoxaden.

Preferred herbicides of group B2 are dimethenamide, dimethenamide-P, napropamide, pethoxamid, propyzamide, diflufenican, flufenacet, mefenacet, picolinafen, propanil, acetochlor, alachlor, butachlor, metazachlor, metolachlor, S-metolachlor, pretilachlor, thenylchlor, asulam, carbetamide, desmedipham, phenmedipham, esprocarb, molinate, prosulfocarb, thiobencarb, amidosulfuron, chlorimuron-ethyl, cyclosulfamuron, ethoxysulfuron, flupyrsulfuron-methyl-sodium, foramsulfuron, iodosulfuron-methyl-sodium, mesosulfuron-methyl, nicosulfuron, orthosulfamuron, prosulfuron, pyrazosulfuron-ethyl, rimsulfuron, trifloxysulfuron (sodium), flucarbazone-sodium, propoxycarbazone-sodium, thiencarbazone-methyl, florasulam, metosulam, penoxsulam, metsulfuron-methyl, sulfosulfuron, thifensulfuron-methyl, tribenuron-methyl, tritosulfuron, pyroxsulam.

Particularly preferred herbicides of group B2 are dimethenamide-P, napropamide, diflufenican, flufenacet, mefenacet, acetochlor, metazachlor, S-metolachlor, asulam, desmedipham, phenmedipham, molinate, prosulfocarb, amidosulfuron, ethoxysulfuron, foramsulfuron, iodosulfuron-methyl-sodium, mesosulfuron-methyl, flucarbazone-sodium, propoxycarbazone-sodium, thiencarbazone-methyl, florasulam, metosulam, metsulfuron-methyl, sulfosulfuron, thifensulfuron-methyl, tribenuron-methyl, tritosulfuron, pyroxsulam.

Preferred herbicides of group B3 are bromoxynil and ioxynil.

Preferred herbicides of group B4 are benzofenap, topramezone, pyrasulfotole, isoxaflutole, imazamox, imazethapyr, oxadiargyl, oxadiazon, amicarbazone, carfentrazone-ethyl, sulfentrazone, uniconazole, cafenstrole, fentrazamide, 3-(3-chloro-5-{[1-methyl-3-(trifluoromethyl)-1H-pyrazol-5-yl]oxy}phenoxy)-1-methyl-5-(trifluoromethyl)-1H-pyrazole, 3-(3-iodo-5-{[1-methyl-3-(trifluoromethyl)-1H-pyrazol-5-yl]oxy}phenoxy)-1-methyl-5-(trifluoromethyl)-1H-pyrazole, 1-ethyl-3-(3-fluoro-5-{[1-methyl-3-(trifluoromethyl)-1H-pyrazol-5-yl]oxy}phenoxy)-5-(trifluoromethyl)-1H-pyrazole, pyraflufen-ethyl.

Particularly preferred herbicides of group B4 are pyrasulfotole, isoxaflutole, oxadiargyl, oxadiazon, amicarbazone, fentrazamide, 3-(3-chloro-5-{[1-methyl-3-(trifluoromethyl)-1H-pyrazol-5-yl]oxy}phenoxy)-1-methyl-5-(trifluoromethyl)-1H-pyrazole, 3-(3-iodo-5-{[1-methyl-3-(trifluoromethyl)-1H-pyrazol-5-yl]oxy}phenoxy)-1-methyl-5-(trifluoromethyl)-1H-pyrazole, 1-ethyl-3-(3-fluoro-5-{[1-methyl-3-(trifluoromethyl)-1H-pyrazol-5-yl]oxy}phenoxy)-5-(trifluoromethyl)-1H-pyrazole, pyraflufen-ethyl, imazamox.

Preferred herbicides of group B5 are aminopyralid, benazolin, benfuresate, bentazone, cinidon-ethyl, clomazone, diquat dibromide, ethofumesate, flumiclorac-pentyl, flumioxazin, flurtamone, oxaziclomefone, pendimethalin, pyridate and trifluralin. Particularly preferred herbicides of group B5 are aminopyralid, benfuresate, ethofumesate, flurtamone and oxaziclomefone.

Preferred herbicides of group B6 are dicamba, clopyralid, fluroxypyr, picloram, triclopyr, quinclorac.

Preferred herbicides of group B7 are anilofos, glufosinate-ammonium and L-glufosinate-ammonium, glyphosate, glyphosate-isopropyl-ammonium, glyphosate-ammonium, glyphosate-trimesium (=sulfosate), glyphosate-diammonium, glyphosate-potassium.

Preferred herbicides of group B8 are acifluorfen-sodium, aclonifen, fluoroglycofen-ethyl, oxyfluorfen, bifenox, dichlorprop-P, mecoprop-P, 2,4-D, MCPA, clodinafop-propargyl, cyhalofop-butyl, diclofop-methyl, diclofop-P-methyl, fenoxaprop-P-ethyl, fluazifop-P-butyl, quizalofop-P.

Particularly preferred herbicides of group B8 are aclonifen, diclofop-methyl, diclofop-P-methyl, fenoxaprop-P-ethyl, MCPA, 2,4-D, clodinafop-ethyl.

Particularly preferred herbicides of group B9 are bispyribac (sodium), pyriftalid, bromacil, lenacil, 2-chloro-4-fluoro-5-[3-methyl-2,6-dioxo-4-(trifluoromethyl)-3,6-dihydropyrimidin-1(2H)-yl]-N-[methyl(1-methylethyl)-sulfamoyl]benzamide.

Preferred herbicides of group B9 are bispyribac (sodium), bromacil.

Preferred herbicides of group B10 are cumyluron, daimuron, diuron, isoproturon, diflufenzopyr.

Preferred herbicides of group B11 are atrazine, simazine, terbuthylazine, ametryn, terbutryn, metamitron, metribuzin.

Particularly preferred herbicides of group B11 are metamitron, metribuzin, terbuthylazine.

In the herbicidal compositions according to the invention, the application rate of the herbicides of the general formula (I) (component A) is usually from 1 to 500 g of active ingredient (a.i.) per hectare, preferably from 2 to 300 g of a.i./ha, particularly preferably from 3 to 200 g of a.i./ha. The application rate of the herbicides of component B is usually from 1 to 5000 g of active ingredient per hectare, preferably from 2 to 3000 g of a.i./ha, particularly preferably from 3 to 2000 g of a.i./ha. The application rate of the safeners of component C is usually from 1 to 500 g of active ingredient per hectare, preferably from 2 to 400 g of a.i./ha, particularly preferably from 3 to 300 g of a.i./ha.

By applying the herbicidal compositions according to the invention, a very broad spectrum of harmful plants, for example annual and perennial mono- or dicotyledonous weeds and unwanted crop plants, is controlled in pre-emergence and post-emergence methods. The herbicidal compositions according to the invention are particularly suitable for use in crops such as cereals, corn, rice, soybean, oilseed rape, sugar beet, cotton, sugar cane, and also for use in perennial crops, plantations and on non-crop land. They are likewise highly suitable for use in transgenic crops of corn, cereals, sugar beet, rice, cotton and *Glycine max*. (e.g. RR soybeans or LL soybeans) and crossbreeds thereof), *Phaseolus, Pisum, Vicia* and *Arachis*, or vegetable crops from various botanical groups such as potato, leek, cabbage, carrot, tomato, onion, and also perennial and plantation crops such as pome fruit and stone fruit, soft fruit, wine, Hevea, bananas, sugar cane, coffee, tea, citrus, nut plantations, lawn, palm crops and forest crops. For the use of the herbicide-safener combinations (A)+(B) according to the invention, these crops are likewise preferred, particular preference being given to use in cereals (e.g. wheat, barley, rye, oats), rice, corn, milletsorghum, sugar beet, sugar cane, sunflower, oilseed rape and cotton. The herbicide-safener combinations (A)+(B) can also be used in tolerant and non-tolerant mutant crops and tolerant and non-tolerant transgenic crops, preferably of corn, rice, cereals, cotton, sugar beet and soybean, e.g. those resistant to imidazolinone herbicides, atrazine, glufosinate, glyphosate, 2,4 D, dicamba and herbicides from the group of the inhibitors of hydroxyphenylpyruvate dioxygenase, such as sulcotrione, mesotrione, tembotrione, tefuryltrione, benzobicyclon, bicyclopyrone and ketospiradox.

Herbicidally effective amount in the sense of the invention is an amount of one or more herbicides suitable for having an adverse impact on plant growth. An "antidotically active amount" in the context of the invention means an amount of one or more safeners suitable for reducing the phytotoxic effect of active compounds of crop protection compositions (for example of herbicides) on crop plants.

According to their properties, the safeners (C) present in the herbicidal compositions according to the invention can each also be used for pretreatment of the seed of the crop plant (for example for dressing of the seed) or introduced into the seed furrows prior to sowing or employed together with the herbicide prior to or after emergence of the plants. Pre-emergence treatment includes both the treatment of the area under cultivation (including any water present in the area under cultivation, for example in the case of applications to rice) prior to sowing and the treatment of the areas under cultivation in which seeds have been sown but which are not yet covered by growing plants. Preference is given to application together with the herbicide. For this purpose, it is possible to use tank-mixes or ready-made formulations.

In a preferred embodiment, the seed (for example grains, seeds or vegetative propagation organs such as tubers or budded parts of shoots) or seedlings are pretreated with the safeners (C), optionally in combination with other agrochemically active compounds. For pretreatment of the seed, the active compounds can be applied to the seed, for example by dressing, or the active compounds and the seed can be added to water or other solvents, and the active compounds can be taken up, for example, by adsorption or diffusion in a dipping process or by swelling or pre-germination. For pretreatment of seedlings, the young plants can be contacted with the safeners, optionally in combination with other active agrochemical compounds, for example by spraying, dipping or watering, and then transplanted and optionally aftertreated with the herbicides (A) and (B).

The seed or seedlings can be treated with the safeners (C) alone or together with other active agrochemical compounds—such as fungicides, insecticides or plant fortifiers, fertilizers or swelling and germination accelerators. After the pretreatment application, the safeners may subsequently be applied once again before, after or together with one or more herbicides of the formula (I) (A) and herbicides (B), possibly also in combination with other known herbicides. The pretreatment of the seed or seedlings can achieve improved long-term action of the safeners.

The present invention thus further provides a method for controlling unwanted plants in plant crops, which is characterized in that components (A), (B) and optionally (C) of the herbicidal compositions according to the invention are deployed, for example separately or together, on the plants (for example harmful plants such as mono- or dicotyledonous weeds or unwanted crop plants), the seed (for example grains, seeds or vegetative propagation organs such as tubers or budded parts of shoots) or the area on which the plants grow (for example the area under cultivation). One or more safeners (C) may be applied before, after or simultaneously with the herbicide(s) of the general formula (I) (A) and the herbicides (B) to the plants, the seed or the area on which the plants grow (for example the area under cultivation). In a preferred embodiment, the safeners (C) are used for seed treatment.

Unwanted plants are understood to mean all plants which grow at sites where they are unwanted. These may, for example, be harmful plants (for example monocotyledonous or dicotyledonous weeds or unwanted crop plants), including, for example, those which are resistant to certain active herbicidal compounds, such as glyphosate, atrazine, glufosinate or imidazolinone herbicides.

Monocotyledonous weeds are classified, for example in the genera *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera*. Dicotyledonous weeds are classified, for example, in the genera *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum, Euphorbia*.

The invention also provides for the use of the herbicidal compositions according to the invention for controlling unwanted vegetation, preferably in plant crops.

The herbicidal compositions according to the invention can be prepared by known processes, for example as mixed formulations of the individual components, if appropriate with further active compounds, additives and/or customary formulation auxiliaries, which combinations are then applied in a customary manner diluted with water, or as tank mixes by joint dilution of the individual components, formulated separately or formulated partially separately, with water. Also possible is the split application of the separately formulated or partially separately formulated individual components. It is also possible to apply the individual components or the herbicidal compositions in a plurality of portions (sequential application), for example pre-emergence applications followed by post-emergence applications or early post-emergence applications followed by medium or late post-emergence applications. Preference is given to the joint or immediately successive application of the active compounds in the respective combination.

The herbicidal compositions according to the invention can also be used for control of harmful plants in crops of genetically modified plants which are known or are yet to be developed.

In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material. Other particular properties may be tolerance or resistance to abiotic stressors, for example heat, low temperatures, drought, salinity and ultraviolet radiation.

Preference is given to the use of the herbicidal compositions according to the invention in economically important transgenic crops of useful plants and ornamentals, for example of cereals such as wheat, barley, rye, oats, millet-sorghum, rice, cassava and corn, or else crops of sugar beet, cotton, soybean, oilseed rape, potato, tomato, peas and other vegetables.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of:

genetic modifications of crop plants for the purpose of modifying the starch synthesized in the plants (for example WO 92011376, WO 92014827, WO 91019806), transgenic crop plants which are resistant to particular herbicides of the glufosinate type (cf., for example, EP-A-0242236, EP-A-242246) or glyphosate type (WO 9200377) or of the sulfonylurea type (EP-A-0257993, U.S. Pat. No. 5,013,659), transgenic crop plants, for example cotton, with the ability to produce *Bacillus thuringiensis* toxins (Bt toxins), which make the plants resistant to particular pests (EP-A-0142924, EP-A-0193259).

transgenic crop plants with a modified fatty acid composition (WO 91/3972).

genetically modified crop plants with novel plant constituents or secondary metabolites, for example novel phytoalexins, which bring about an increased disease resistance (EPA 309862, EPA0464461)

genetically modified plants with reduced photorespiration, which feature higher yields and higher stress tolerance (EPA 0305398).

transgenic crop plants which produce pharmaceutically or diagnostically important proteins ("molecular pharming")

transgenic crop plants which feature higher yields or better quality transgenic crop plants which feature a combination, for example, of the abovementioned novel properties ("gene stacking")

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431).

For such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is possible firstly to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized may be localized in any desired compartment of the plant cell. However, in order to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants.

For instance, it is possible to obtain transgenic plants whose properties are altered by overexpression, suppression or inhibition of homologous (=natural) genes or gene sequences, or expression of heterologous (=foreign) genes or gene sequences.

Preferably the compositions according to the invention can be used in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds.

On employment of the compositions according to the invention in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the compositions according to the invention for control of harmful plants in transgenic crop plants.

Preference is given to the use of the compositions according to the invention in economically important transgenic crops of useful plants and ornamentals, for example of cereals (e.g. wheat, barley, rye, oats), milletsorghum, rice, cassava and corn, or else crops of sugar beet, cotton, soybean, oilseed rape, potato, tomato, peas and other vegetable crops.

The invention therefore also provides for the use of the compositions according to the invention for control of harmful plants in transgenic crop plants or crop plants having tolerance through selective breeding.

The herbicides (A), (B) and the safeners (C) can be converted together or separately to customary formulations, for example for application by spraying, watering, sprinkling and seed dressing, such as solutions, emulsions, suspensions, powders, foams, pastes, granules, aerosols, active ingredient-impregnated natural and synthetic substances, microencapsulations in polymeric substances. The formulations may comprise the customary auxiliaries and additives.

These formulations are produced in a known manner, for example by mixing the active compounds with extenders, i.e. liquid solvents, pressurized liquefied gases and/or solid carriers, optionally with use of surfactants, i.e. emulsifiers and/or dispersants and/or foam formers.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and the ethers and esters thereof, ketones such as acetone, methyl ethyl ketone, methyl isobutyl ketone or cyclohexanone, strongly polar solvents such as dimethylformamide or dimethyl sulfoxide, and water.

Useful solid carriers include: for example ammonium salts and ground natural minerals, such as kaolins, clays, talc, chalk, quartz, attapulgite, montmorillonite or diatomaceous earth, and ground synthetic minerals, such as finely divided silica, alumina and silicates; useful solid carriers for granules include: for example crushed and fractionated natural rocks, such as calcite, marble, pumice, sepiolite, dolomite and synthetic granules of inorganic and organic flours, and granules of organic material, such as sawdust, coconut shells, corn cobs and tobacco stalks; useful emulsifiers and/or foam formers include: for example nonionic and anionic emulsifiers, such as polyoxyethylene fatty acid esters, polyoxyethylene fatty alcohol ethers, e.g. alkylaryl polyglycol ethers, alkylsulfonates, alkylsulfates, arylsulfonates and protein hydrolyzates; useful dispersants include: for example lignosulfite waste liquors and methylcellulose.

In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

The formulations contain generally between 0.1 and 95 percent by weight of active ingredient, preferably between 0.5 and 90% by weight.

As such or in their formulations, the herbicides (A), (B) and the safeners (C) can also be used as a mixture with other agrochemically active compounds for controlling unwanted vegetation, for example for controlling weeds or for controlling unwanted crop plants, finished formulations or tank mixes, for example, being possible.

Also possible are mixtures with other known active compounds such as fungicides, insecticides, acaricides, nematicides, bird antifeedants, plant nutrients and soil improvers, and likewise with additives and formulation auxiliaries customary in crop protection.

The herbicides (A), (B) and the safeners (C) can be used as such, in the form of their formulations or the use forms prepared therefrom by further dilution, such as ready-to-use solutions, suspensions, emulsions, powders, pastes and granules. Application is typically accomplished, for example, by watering, sprinkling, spraying, broadcasting.

The active compounds can be deployed on the plants, plant parts, seed or area under cultivation (farmland), preferably on the seed or the green plants and plant parts, and optionally additionally to the farmland. One means of application is the co-deployment of the active compounds in the form of tank-mixes, by mixing the optimally formulated concentrated formulations of the individual active compounds together in the tank with water and deploying the spray liquor obtained.

A co-formulation of the combination according to the invention of active compounds (A), (B) and (C) has the advantage of easier applicability, because the amounts of the components can already be set in the optimal ratio with respect to one another. Moreover, the auxiliaries in the formulation can be optimized to one another.

For application, the formulations present in commercial form are, if appropriate, diluted in a customary manner, for example in the case of wettable powders, emulsifiable concentrates, dispersions and water-dispersible granules with water. Preparations in the form of dusts, granules for soil application or granules for sowing and sprayable solutions are usually not diluted further with other inert substances prior to application.

BIOLOGICAL EXAMPLES

Test Conditions in the Greenhouse Trial

The weed seeds were sown in pots (diameter 8 cm) with sandy loam soil and germinated under optimum conditions.

The herbides were applied by the post-emergence method onto the pots with the cultures, at a spray volume of 300 l/ha. The herbicides were applied on their own and in combination. The trial was conducted in a greenhouse under optimum growth conditions. The herbicidal effects were assessed visually by comparison of untreated and treated plants. The percentages mean: 0%=no effects, 100%=the plants die off completely). The percentages are used to calculate interactions between individual treatments and combination treatment according to S. R. Colby, Weeds 15, pages 20 to 22 (1967).

The results are given in the tables below.

Test Conditions in the Field Trial

The tests were conducted outdoors (plot trials, 10 m² per plot, 2 repetitions, spray application with 200-300 liters of water per hectare). Crops and broad-leaved weeds/weed grasses were sown under customary field conditions. In addition, a natural weed flora also appeared. Application was by the post-emergence method. The application rates of the herbicidally active compounds applied on their own or in combinations are likewise shown in the tables below. Evaluations were by visual scoring (using a 0-100% scale) after application by comparison of treated and untreated test variants. The results (as a mean for all plants/plot and for 2 repetitions) are reported in the table below.

Seed Treatment

Seed grains of crop plants were mixed and shaken well in bottles with the safeners formulated as suspension or emulsion concentrates and water, such that the seed grains were coated homogeneously with the formulation of the respective safener. The seed grains or the plants after emergence were then treated with herbicides by the pre-emergence or post-emergence method. Here, numerous herbicide/safener compositions according to the invention showed good compatibility with the crop plants and simultaneously have good herbicidal activity against a broad spectrum of harmful plants.

The abbreviations denote:
a.i.=active ingredient
$E^C$=expected value according to Colby ($E^C$=A+B−A×B100)
$\Delta$=difference (%) of the measured value to the expected value (%) (measured value minus expected value)
Evaluation:
measured value E is greater than $E^C$:→synergism (+Δ)
measured value E equals $E^C$:→additive effect
measured value E is smaller than $E^C$:→antagonism (−Δ)

TABLE 5-01

| | Greenhouse | |
|---|---|---|
| Active compound | Dosage [g of a.i./ha] | Activity [%] against *Avena fatua* |
| A1-2 | 2 | 0 |
| fenoxaprop-P-ethyl | 25 | 0 |
| A1-2 + fenoxaprop-P-ethyl | 2 + 25 | 15 ($E^C$ = 0, Δ = 15) |

TABLE 5-02

| | Greenhouse | |
|---|---|---|
| Active compound | Dosage [g of a.i./ha] | Activity [%] against *Viola tricolor* |
| A1-2 | 2 | 60 |
| fenoxaprop-P-ethyl | 25 | 0 |
| A1-2 + fenoxaprop-P-ethyl | 2 + 25 | 80 ($E^C$ = 60, Δ = 20) |

TABLE 5-03

| | Greenhouse | |
|---|---|---|
| Active compound | Dosage [g of a.i./ha] | Activity [%] against *Phalaris minor* |
| A1-2 | 2 | 0 |
| fenoxaprop-P-ethyl | 25 | 15 |
| A1-2 + fenoxaprop-P-ethyl | 2 + 25 | 30 ($E^C$ = 15, Δ = 15) |

TABLE 5-04

| | Field | |
|---|---|---|
| Active compound | Dosage [g of a.i./ha] | Activity [%] against *Galium aparine* |
| A1-2 | 25 | 70 |
| bromoxynil | 210 | 13 |
| A1-2 + bromoxynil | 25 + 210 | 100 ($E^C$ = 74, Δ = 26) |

TABLE 5-05

| | Greenhouse | |
|---|---|---|
| Active compound | Dosage [g of a.i./ha] | Activity [%] against *Avena fatua* |
| A1-7 | 3 | 0 |
| fenoxaprop-P-ethyl | 12.5 | 0 |
| A1-7 + fenoxaprop-P-ethyl | 3 + 12.5 | 20 ($E^C$ = 0, Δ = 20) |

TABLE 5-06

| | Greenhouse | |
|---|---|---|
| Active compound | Dosage [g of a.i./ha] | Activity [%] against *Papaver rhoeas* |
| A1-7 | 3 | 60 |
| fenoxaprop-P-ethyl | 12.5 | 20 |
| A1-7 + fenoxaprop-P-ethyl | 3 + 25 | 85 ($E^C$ = 68, Δ = 17) |

TABLE 5-07

| | Greenhouse | |
|---|---|---|
| Active compound | Dosage [g of a.i./ha] | Activity [%] against *Avena fatua* |
| A1-7 | 3 | 0 |
| fenoxaprop-P-ethyl | 12.5 | 0 |
| A1-7 + fenoxaprop-P-ethyl | 3 + 25 | 10 ($E^C$ = 0, Δ = 10) |

TABLE 5-08

| | Greenhouse | |
|---|---|---|
| Active compound | Dosage [g of a.i./ha] | Activity [%] against *Polygonum convolvulus* |
| A1-7 | 3 | 10 |
| fenoxaprop-P-ethyl | 25 | 0 |
| A1-7 + fenoxaprop-P-ethyl | 3 + 25 | 20 ($E^C = 10$, $\Delta = 10$) |

TABLE 5-09

| | Greenhouse | |
|---|---|---|
| Active compound | Dosage [g of a.i./ha] | Activity [%] against *Viola tricolor* |
| A1-7 | 3 | 50 |
| fenoxaprop-P-ethyl | 12.5 | 15 |
| A1-7 + fenoxaprop-P-ethyl | 3 + 12.5 | 85 ($E^C = 58$, $\Delta = 28$) |

TABLE 5-10

| | Field | |
|---|---|---|
| Active compound | Dosage [g of a.i./ha] | Activity [%] against *Sida spinosa* |
| A1-9 | 10 | 60 |
| glufosinate-ammonium | 125 | 50 |
| A1-9 + glufosinate-ammonium | 10 + 125 | 95 ($E^C = 80$, $\Delta = 15$) |

TABLE 5-11

| | Field | |
|---|---|---|
| Active compound | Dosage [g of a.i./ha] | Activity [%] against *Sida spinosa* |
| A1-9 | 10 | 60 |
| glyphosate-potassium | 200 | 30 |
| A1-9 + glyphosate-potassium | 10 + 200 | 85 ($E^C = 72$, $\Delta = 13$) |

TABLE 5-12

| | Field | |
|---|---|---|
| Active compound | Dosage [g of a.i./ha] | Activity [%] against *Cassia obtusifolia* |
| A1-9 | 20 | 0 |
| glyphosate | 200 | 65 |
| A1-9 + glyphosate | 20 + 200 | 85 ($E^C = 65$, $\Delta = 20$) |

TABLE 5-13

| | Field | |
|---|---|---|
| Active compound | Dosage [g of a.i./ha] | Activity [%] against *Portulaca oleracea* |
| A1-9 | 20 | 43 |
| atrazine | 250 | 25 |
| A1-9 + atrazine | 20 + 250 | 100 ($E^C = 57$, $\Delta = 43$) |

TABLE 5-14

| | Field | |
|---|---|---|
| Active compound | Dosage [g of a.i./ha] | Activity [%] against *Portulaca oleracea* |
| A1-9 | 20 | 43 |
| foramsulfuron | 16 | 0 |
| A1-9 + foramsulfuron | 20 + 16 | 85 ($E^C = 43$, $\Delta = 42$) |

TABLE 5-15

| | Field | |
|---|---|---|
| Active compound | Dosage [g of a.i./ha] | Activity [%] against *Portulaca oleracea* |
| A1-9 | 20 | 43 |
| mesotrione | 25 | 0 |
| A1-9 + mesotrione | 20 + 25 | 70 ($E^C = 43$, $\Delta = 27$) |

TABLE 5-16

| | Field | |
|---|---|---|
| Active compound | Dosage [g of a.i./ha] | Activity [%] against *Portulaca oleracea* |
| A1-9 | 20 | 43 |
| metribuzin | 50 | 0 |
| A1-9 + metribuzin | 20 + 50 | 75 ($E^C = 43$, $\Delta = 32$) |

TABLE 5-17

| | Field | |
|---|---|---|
| Active compound | Dosage [g of a.i./ha] | Activity [%] against *Abutilon theophrasti* |
| A1-9 | 20 | 78 |
| dimethenamide-P | 500 | 25 |
| A1-9 + dimethenamide-P | 20 + 500 | 85 ($E^C = 79$, $\Delta = 6$) |

TABLE 5-18

| | Field | |
|---|---|---|
| Active compound | Dosage [g of a.i./ha] | Activity [%] against *Portulaca oleracea* |
| A1-9 | 20 | 43 |
| bicyclopyrone | 25 | 23 |
| A1-9 + bicyclopyrone | 20 + 25 | 90 ($E^C = 56$, $\Delta = 34$) |

TABLE 5-19

| | Field | |
|---|---|---|
| Active compound | Dosage [g of a.i./ha] | Activity [%] against *Portulaca oleracea* |
| A1-9 | 20 | 43 |
| nicosulfuron | 20 | 30 |
| A1-9 + nicosulfuron | 20 + 20 | 68 ($E^C = 60$, $\Delta = 8$) |

TABLE 5-20

Field

| Active compound | Dosage [g of a.i./ha] | Activity [%] against *Portulaca oleracea* |
|---|---|---|
| A1-9 | 20 | 43 |
| rimsulfuron | 6 | 0 |
| A1-9 + rimsulfuron | 20 + 6 | 68 ($E^C$ = 43, Δ = 25) |

TABLE 5-21

Field

| Active compound | Dosage [g of a.i./ha] | Activity [%] against *Sida spinosa* |
|---|---|---|
| A1-9 | 10 | 60 |
| metribuzin | 50 | 25 |
| A1-9 + metribuzin | 10 + 50 | 79 ($E^C$ = 60, Δ = 19) |

TABLE 5-22

Field

| Active compound | Dosage [g of a.i./ha] | Activity [%] against *Portulaca oleracea* |
|---|---|---|
| A1-9 | 10 | 38 |
| aclonifen | 1200 | 0 |
| A1-9 + aclonifen | 10 + 1200 | 83 ($E^C$ = 38, Δ = 45) |

TABLE 5-23

Field

| Active compound | Dosage [g of a.i./ha] | Activity [%] against *Setaria viridis* |
|---|---|---|
| A1-9 | 10 | 15 |
| topramezone | 9 | 30 |
| A1-9 + topramezone | 10 + 9 | 75 ($E^C$ = 40, Δ = 35) |

TABLE 5-24

Field

| Active compound | Dosage [g of a.i./ha] | Activity [%] against *Cassia obtusifolia* |
|---|---|---|
| A1-9 | 20 | 0 |
| indaziflam | 25 | 65 |
| A1-9 + indaziflam | 20 + 25 | 83 ($E^C$ = 65, Δ = 18) |

TABLE 5-25

Field

| Active compound | Dosage [g of a.i./ha] | Activity [%] against *Cassia obtusifolia* |
|---|---|---|
| A1-9 | 25 | 65 |
| bromoxynil | 210 | 10 |
| A1-9 + bromoxynil | 25 + 210 | 90 ($E^C$ = 69, Δ = 22) |

TABLE 5-26

Field

| Active compound | Dosage [g of a.i./ha] | Activity [%] against *Setaria viridis* |
|---|---|---|
| A1-9 | 25 | 7 |
| MCPA | 280 | 0 |
| A1-9 + MCPA | 25 + 280 | 95 ($E^C$ = 75, Δ = 20) |

TABLE 5-27

Greenhouse

| Active compound | Dosage [g of a.i./ha] | Activity [%] against *Setaria viridis* |
|---|---|---|
| A1-23 | 2 | 50 |
| lenacil | 8 | 0 |
| A1-23 + lenacil | 2 + 8 | 60 ($E^C$ = 50, Δ = 10) |

TABLE 5-28

Greenhouse

| Active compound | Dosage [g of a.i./ha] | Activity [%] against *Bidens pilosa* |
|---|---|---|
| A1-23 | 2 | 45 |
| lenacil | 4 | 0 |
| A1-23 + lenacil | 2 + 4 | 70 ($E^C$ = 45, Δ = 25) |

TABLE 5-29

Greenhouse

| Active compound | Dosage [g of a.i./ha] | Activity [%] against *Ambrosia artemisiifolia* |
|---|---|---|
| A1-23 | 1 | 10 |
| lenacil | 16 | 0 |
| A1-23 + lenacil | 1 + 16 | 45 ($E^C$ = 10, Δ = 35) |

TABLE 5-30

Greenhouse

| Active compound | Dosage [g of a.i./ha] | Activity [%] against *Pharbitis purpurea* |
|---|---|---|
| A1-23 | 1 | 45 |
| lenacil | 4 | 0 |
| A1-23 + lenacil | 1 + 4 | 75 ($E^C$ = 45, Δ = 30) |

TABLE 5-31

Greenhouse

| Active compound | Dosage [g of a.i./ha] | Activity [%] against *Setaria viridis* |
|---|---|---|
| A1-23 | 2 | 50 |
| lenacil | 8 | 0 |
| A1-23 + lenacil | 2 + 8 | 70 ($E^C$ = 50, Δ = 20) |

TABLE 5-32

Greenhouse

| Active compound | Dosage [g of a.i./ha] | Activity [%] against *Ambrosia artemisiifolia* |
|---|---|---|
| A1-23 | 1 | 0 |
| lenacil | 4 | 0 |
| A1-23 + lenacil | 1 + 4 | 25 ($E^C = 0$, $\Delta = 25$) |

TABLE 5-33

Greenhouse

| Active compound | Dosage [g of a.i./ha] | Activity [%] against *Bidens pilosa* |
|---|---|---|
| A1-23 | 1 | 35 |
| lenacil | 4 | 0 |
| A1-23 + lenacil | 1 + 4 | 65 ($E^C = 35$, $\Delta = 30$) |

TABLE 5-34

Greenhouse

| Active compound | Dosage [g of a.i./ha] | Activity [%] against *Pharbitis purpurea* |
|---|---|---|
| A1-23 | 2 | 45 |
| lenacil | 4 | 0 |
| A1-23 + lenacil | 2 + 4 | 75 ($E^C = 45$, $\Delta = 30$) |

TABLE 5-35

Greenhouse

| Active compound | Dosage [g of a.i./ha] | Activity [%] against *Digitaria sanguinalis* |
|---|---|---|
| A1-23 | 1 | 10 |
| lenacil | 4 | 0 |
| A1-23 + lenacil | 1 + 4 | 40 ($E^C = 10$, $\Delta = 30$) |

TABLE 5-36

Greenhouse

| Active compound | Dosage [g of a.i./ha] | Activity [%] against *Digitaria sanguinalis* |
|---|---|---|
| A1-24 | 6 | 50 |
| pendimethalin | 50 | 0 |
| A1-24 + pendimethalin | 6 + 50 | 80 ($E^C = 50$, $\Delta = 30$) |

TABLE 5-37

Greenhouse

| Active compound | Dosage [g of a.i./ha] | Activity [%] against *Polygonum convolvulus* |
|---|---|---|
| A1-24 | 6 | 0 |
| pendimethalin | 100 | 0 |
| A1-24 + pendimethalin | 6 + 100 | 30 ($E^C = 0$, $\Delta = 30$) |

TABLE 5-38

Greenhouse

| Active compound | Dosage [g of a.i./ha] | Activity [%] against *Centaurea cyanis* |
|---|---|---|
| A1-26 | 3 | 40 |
| pinoxaden | 5 | 0 |
| A1-26 + pinoxaden | 3 + 5 | 60 ($E^C = 40$, $\Delta = 20$) |

TABLE 5-39

Greenhouse

| Active compound | Dosage [g of a.i./ha] | Activity [%] against *Papaver rhoeas* |
|---|---|---|
| A1-26 | 6 | 50 |
| pinoxaden | 5 | 0 |
| A1-26 + pinoxaden | 6 + 5 | 70 ($E^C = 50$, $\Delta = 20$) |

TABLE 5-40

Greenhouse

| Active compound | Dosage [g of a.i./ha] | Activity [%] against *Centaurea cyanis* |
|---|---|---|
| A1-26 | 6 | 60 |
| pinoxaden | 5 | 15 |
| A1-26 + pinoxaden | 6 + 5 | 85 ($E^C = 66$, $\Delta = 19$) |

TABLE 5-41

Greenhouse

| Active compound | Dosage [g of a.i./ha] | Activity [%] against *Papaver rhoeas* |
|---|---|---|
| A1-26 | 3 | 30 |
| pinoxaden | 10 | 10 |
| A1-26 + pinoxaden | 3 + 10 | 60 ($E^C = 37$, $\Delta = 23$) |

TABLE 5-42

Greenhouse

| Active compound | Dosage [g of a.i./ha] | Activity [%] against *Viola tricolor* |
|---|---|---|
| A1-26 | 3 | 50 |
| pinoxaden | 10 | 0 |
| A1-26 + pinoxaden | 3 + 10 | 70 ($E^C = 50$, $\Delta = 15$) |

TABLE 5-43

Greenhouse

| Active compound | Dosage [g of a.i./ha] | Activity [%] against *Setaria viridis* |
|---|---|---|
| A1-33 | 2 | 75 |
| isoproturon | 200 | 10 |
| A1-33 + isoproturon | 2 + 200 | 95 ($E^C = 78$, $\Delta = 18$) |

TABLE 5-44

Greenhouse

| Active compound | Dosage [g of a.i./ha] | Activity [%] against *Polygonum convolvulus* |
|---|---|---|
| A1-33 | 4 | 0 |
| isoproturon | 200 | 0 |
| A1-33 + isoproturon | 4 + 200 | 20 ($E^C = 0$, $\Delta = 20$) |

TABLE 5-45

Greenhouse

| Active compound | Dosage [g of a.i./ha] | Activity [%] against *Brachiaria platyphylla* |
|---|---|---|
| A1-36 | 2 | 25 |
| imazamox | 2 | 10 |
| A1-36 + imazamox | 2 + 2 | 65 ($E^C = 33$, $\Delta = 32$) |

TABLE 5-46

Greenhouse

| Active compound | Dosage [g of a.i./ha] | Activity [%] against *Bidens pilosa* |
|---|---|---|
| A1-36 | 2 | 45 |
| imazamox | 1 | 10 |
| A1-36 + imazamox | 2 + 1 | 70 ($E^C = 51$, $\Delta = 19$) |

TABLE 5-47

Greenhouse

| Active compound | Dosage [g of a.i./ha] | Activity [%] against *Bidens pilosa* |
|---|---|---|
| A1-36 | 4 | 30 |
| imazamox | 2 | 20 |
| A1-36 + imazamox | 4 + 2 | 65 ($E^C = 44$, $\Delta = 21$) |

TABLE 5-48

Field

| Active compound | Dosage [g of a.i./ha] | Activity [%] against *Amaranthus retroflexus* |
|---|---|---|
| A1-36 | 50 | 0 |
| atrazine | 560 | 60 |
| A1-36 + atrazine | 50 + 560 | 92 ($E^C = 60$, $\Delta = 32$) |

TABLE 5-49

Greenhouse

| Active compound | Dosage [g of a.i./ha] | Activity [%] against *Avena fatua* |
|---|---|---|
| A1-44 | 4 | 0 |
| fenoxaprop-P-ethyl | 25 | 0 |
| A1-44 + fenoxaprop-P-ethyl | 4 + 25 | 15 ($E^C = 0$, $\Delta = 15$) |

TABLE 5-50

Greenhouse

| Active compound | Dosage [g of a.i./ha] | Activity [%] against *Centaurea cyanis* |
|---|---|---|
| A1-44 | 8 | 50 |
| fenoxaprop-P-ethyl | 25 | 0 |
| A1-44 + fenoxaprop-P-ethyl | 8 + 25 | 65 ($E^C = 50$, $\Delta = 15$) |

TABLE 5-51

Field

| Active compound | Dosage [g of a.i./ha] | Activity [%] against *Euphorbia heterophylla* |
|---|---|---|
| A1-44 | 25 | 58 |
| atrazine | 1000 | 49 |
| A1-44 + atrazine | 25 + 1000 | 94 ($E^C = 70$, $\Delta = 15$) |

TABLE 5-52

Greenhouse

| Active compound | Dosage [g of a.i./ha] | Activity [%] against *Ambrosia artemisiifolia* |
|---|---|---|
| A1-49 | 4 | 80 |
| thiencarbazone-methyl | 0.25 | 0 |
| A1-49 + thiencarbazone-methyl | 4 + 0.25 | 98 ($E^C = 80$, $\Delta = 18$) |

TABLE 5-53

Field

| Active compound | Dosage [g of a.i./ha] | Activity [%] against *Polygunum convolvulus* |
|---|---|---|
| A1-49 | 25 | 35 |
| bromoxynil | 210 | 30 |
| A1-49 + bromoxynil | 25 + 210 | 78 ($E^C = 55$, $\Delta = 24$) |

TABLE 5-54

Field

| Active compound | Dosage [g of a.i./ha] | Activity [%] against *Lolium multiflorum* |
|---|---|---|
| A1-49 | 25 | 40 |
| MCPA | 280 | 0 |
| A1-49 + MCPA | 25 + 280 | 60 ($E^C = 40$, $\Delta = 20$) |

TABLE 5-55

Greenhouse

| Active compound | Dosage [g of a.i./ha] | Activity [%] against *Brachiaria platyphylla* |
|---|---|---|
| A1-60 | 1 | 0 |
| lenacil | 4 | 0 |
| A1-60 + lenacil | 1 + 4 | 15 ($E^C = 0$, $\Delta = 15$) |

TABLE 5-56

| | Greenhouse | |
|---|---|---|
| Active compound | Dosage [g of a.i./ha] | Activity [%] against *Xanthium strumarium* |
| A1-60 | 1 | 25 |
| lenacil | 4 | 0 |
| A1-60 + lenacil | 1 + 4 | 55 ($E^C$ = 25, Δ = 30) |

TABLE 5-57

| | Greenhouse | |
|---|---|---|
| Active compound | Dosage [g of a.i./ha] | Activity [%] against *Brachiaria platyphylla* |
| A1-60 | 2 | 40 |
| lenacil | 4 | 0 |
| A1-60 + lenacil | 2 + 4 | 65 ($E^C$ = 40, Δ = 25) |

TABLE 5-58

| | Field | |
|---|---|---|
| Active compound | Dosage [g of a.i./ha] | Activity [%] against *Lolium multiflorum* |
| A1-60 | 25 | 15 |
| diflufenican | 120 | 10 |
| A1-60 + diflufenican | 25 + 120 | 50 ($E^C$ = 24, Δ = 27) |

TABLE 5-59

| | Field | |
|---|---|---|
| Active compound | Dosage [g of a.i./ha] | Activity [%] against *Centaurea cyanis* |
| A1-60 | 25 | 45 |
| flufenacet | 240 | 0 |
| A1-60 + flufenacet | 25 + 240 | 63 ($E^C$ = 45, Δ = 18) |

TABLE 5-60

| | Field | |
|---|---|---|
| Active compound | Dosage [g of a.i./ha] | Activity [%] against *Alopecurus myosuroides* |
| A1-60 | 25 | 15 |
| fenoxaprop-P-ethyl | 83 | 30 |
| A1-60 + fenoxaprop-P-ethyl | 25 + 83 | 60 ($E^C$ = 41, Δ = 20) |

TABLE 5-61

| | Field | |
|---|---|---|
| Active compound | Dosage [g of a.i./ha] | Activity [%] against *Galium aparine* |
| A1-60 | 25 | 30 |
| MCPA | 280 | 0 |
| A1-60 + MCPA | 25 + 280 | 65 ($E^C$ = 30, Δ = 35) |

TABLE 5-62

| | Field | |
|---|---|---|
| Active compound | Dosage [g of a.i./ha] | Activity [%] against *Galium aparine* |
| A1-60 | 25 | 73 |
| bromoxynil | 210 | 13 |
| A1-60 + bromoxynil | 25 + 210 | 100 ($E^C$ = 77, Δ = 23) |

TABLE 5-63

| | Field | |
|---|---|---|
| Active compound | Dosage [g of a.i./ha] | Activity [%] against *Euphorbia heterophylla* |
| A1-60 | 25 | 30 |
| atrazine | 1000 | 49 |
| A1-60 + atrazine | 25 + 1000 | 91 ($E^C$ = 64, Δ = 27) |

TABLE 5-64

| | Greenhouse | |
|---|---|---|
| Active compound | Dosage [g of a.i./ha] | Activity [%] against *Brachiaria platyphylla* |
| A1-61 | 6 | 0 |
| dicamba | 25 | 10 |
| A1-61 + dicamba | 6 + 25 | 30 ($E^C$ = 10, Δ = 20) |

TABLE 5-65

| | Greenhouse | |
|---|---|---|
| Active compound | Dosage [g of a.i./ha] | Activity [%] against *Setaria viridis* |
| A1-61 | 3 | 0 |
| dicamba | 25 | 0 |
| A1-61 + dicamba | 3 + 25 | 15 ($E^C$ = 0, Δ = 15) |

TABLE 5-66

| | Field | |
|---|---|---|
| Active compound | Dosage [g of a.i./ha] | Activity [%] against *Veronica hederifolia* |
| A1-61 | 25 | 68 |
| bromoxynil | 210 | 5 |
| A1-61 + bromoxynil | 25 + 210 | 99 ($E^C$ = 70, Δ = 29) |

TABLE 5-67

| | Greenhouse | |
|---|---|---|
| Active compound | Dosage [g of a.i./ha] | Activity [%] against *Brachiaria platyphylla* |
| A1-63 | 8 | 10 |
| lenacil | 800 | 0 |
| A1-63 + lenacil | 8 + 800 | 35 ($E^C$ = 10, Δ = 25) |

TABLE 5-68

| | Greenhouse | |
|---|---|---|
| Active compound | Dosage [g of a.i./ha] | Activity [%] against *Digitaria sanguinalis* |
| A1-63 | 8 | 45 |
| lenacil | 400 | 0 |
| A1-63 + lenacil | 8 + 400 | 80 ($E^C$ = 45, Δ = 35) |

TABLE 5-69

| | Greenhouse | |
|---|---|---|
| Active compound | Dosage [g of a.i./ha] | Activity [%] against *Echinochloa crus-galli* |
| A1-63 | 8 | 85 |
| lenacil | 400 | 0 |
| A1-63 + lenacil | 8 + 400 | 98 ($E^C$ = 85, Δ = 13) |

TABLE 5-70

| | Greenhouse | |
|---|---|---|
| Active compound | Dosage [g of a.i./ha] | Activity [%] against *Setaria viridis* |
| A1-63 | 4 | 50 |
| lenacil | 100 | 0 |
| A1-63 + lenacil | 4 + 100 | 75 ($E^C$ = 50, Δ = 25) |

TABLE 5-71

| | Greenhouse | |
|---|---|---|
| Active compound | Dosage [g of a.i./ha] | Activity [%] against *Bidens pilosa* |
| A1-63 | 8 | 50 |
| lenacil | 400 | 0 |
| A1-63 + lenacil | 8 + 400 | 85 ($E^C$ = 50, Δ = 35) |

TABLE 5-72

| | Greenhouse | |
|---|---|---|
| Active compound | Dosage [g of a.i./ha] | Activity [%] against *Pharbitis purpurea* |
| A1-63 | 4 | 35 |
| lenacil | 100 | 0 |
| A1-63 + lenacil | 4 + 100 | 55 ($E^C$ = 35, Δ = 20) |

TABLE 5-73

| | Greenhouse | |
|---|---|---|
| Active compound | Dosage [g of a.i./ha] | Activity [%] against *Xanthium strumarium* |
| A1-63 | 8 | 80 |
| lenacil | 400 | 0 |
| A1-63 + lenacil | 8 + 400 | 95 ($E^C$ = 80, Δ = 15) |

TABLE 5-74

| | Field | |
|---|---|---|
| Active compound | Dosage [g of a.i./ha] | Activity [%] against *Veronica hederifolia* |
| A1-63 | 25 | 68 |
| bromoxynil | 210 | 5 |
| A1-63 + bromoxynil | 25 + 210 | 93 ($E^C$ = 70, Δ = 23) |

TABLE 5-75

| | Greenhouse | |
|---|---|---|
| Active compound | Dosage [g of a.i./ha] | Activity [%] against *Ambrosia artemisiifolia* |
| A1-66 | 6 | 35 |
| thiencarbazone-methyl | 0.25 | 0 |
| A1-66 + thiencarbazone-methyl | 6 + 0.25 | 80 ($E^C$ = 35, Δ = 45) |

TABLE 5-76

| | Field | |
|---|---|---|
| Active compound | Dosage [g of a.i./ha] | Activity [%] against *Veronica hederifolia* |
| A1-66 | 25 | 75 |
| bromoxynil | 210 | 0 |
| A1-66 + bromoxynil | 25 + 210 | 100 ($E^C$ = 75, Δ = 25) |

TABLE 5-77

| | Greenhouse | |
|---|---|---|
| Active compound | Dosage [g of a.i./ha] | Activity [%] against *Xanthium strumarium* |
| A1-67 | 4 | 0 |
| pendimethalin | 100 | 0 |
| A1-67 + pendimethalin | 4 + 100 | 20 ($E^C$ = 0, Δ = 20) |

TABLE 5-78

| | Greenhouse | |
|---|---|---|
| Active compound | Dosage [g of a.i./ha] | Activity [%] against *Polygonum convolvulus* |
| A1-67 | 4 | 10 |
| pendimethalin | 100 | 0 |
| A1-67 + pendimethalin | 4 + 100 | 30 ($E^C$ = 10, Δ = 20) |

TABLE 5-79

| | Field | |
|---|---|---|
| Active compound | Dosage [g of a.i./ha] | Activity [%] against *Veronica hederifolia* |
| A1-67 | 25 | 75 |
| bromoxynil | 210 | 5 |
| A1-67 + bromoxynil | 25 + 210 | 100 ($E^C$ = 76, Δ = 24) |

TABLE 5-80

Field

| Active compound | Dosage [g of a.i./ha] | Activity [%] against *Setaria viridis* |
|---|---|---|
| A1-67 | 25 | 65 |
| MCPA | 280 | 0 |
| A1-67 + MCPA | 25 + 280 | 83 ($E^C$ = 65, Δ = 18) |

TABLE 5-81

Greenhouse

| Active compound | Dosage [g of a.i./ha] | Activity [%] against *Centaurea cyanis* |
|---|---|---|
| A1-69 | 4 | 65 |
| isoproturon | 100 | 0 |
| A1-69 + isoproturon | 4 + 100 | 85 ($E^C$ = 65, Δ = 20) |

TABLE 5-82

Greenhouse

| Active compound | Dosage [g of a.i./ha] | Activity [%] against *Papaver rhoeas* |
|---|---|---|
| A1-69 | 4 | 10 |
| isoproturon | 200 | 40 |
| A1-69 + isoproturon | 4 + 200 | 80 ($E^C$ = 46, Δ = 34) |

TABLE 5-83

Greenhouse

| Active compound | Dosage [g of a.i./ha] | Activity [%] against *Papaver rhoeas* |
|---|---|---|
| A1-69 | 4 | 10 |
| isoproturon | 200 | 40 |
| A1-69 + isoproturon | 4 + 200 | 80 ($E^C$ = 46, Δ = 34) |

TABLE 5-84

Greenhouse

| Active compound | Dosage [g of a.i./ha] | Activity [%] against *Polygonum convolvulus* |
|---|---|---|
| A1-69 | 4 | 0 |
| isoproturon | 200 | 0 |
| A1-69 + isoproturon | 4 + 200 | 30 ($E^C$ = 0, Δ = 30) |

TABLE 5-85

Field

| Active compound | Dosage [g of a.i./ha] | Activity [%] against *Euphorbia heterophylla* |
|---|---|---|
| A1-69 | 25 | 20 |
| atrazine | 1000 | 49 |
| A1-69 + atrazine | 25 + 1000 | 89 ($E^C$ = 59, Δ = 30) |

TABLE 5-86

Greenhouse

| Active compound | Dosage [g of a.i./ha] | Activity [%] against *Papaver rhoeas* |
|---|---|---|
| A1-74 | 3 | 30 |
| pinoxaden | 10 | 0 |
| A1-74 + pinoxaden | 3 + 10 | 60 ($E^C$ = 30, Δ = 30) |

TABLE 5-87

Greenhouse

| Active compound | Dosage [g of a.i./ha] | Activity [%] against *Papaver rhoeas* |
|---|---|---|
| A1-74 | 3 | 40 |
| pinoxaden | 10 | 50 |
| A1-74 + pinoxaden | 3 + 10 | 90 ($E^C$ = 70, Δ = 20) |

TABLE 5-88

Greenhouse

| Active compound | Dosage [g of a.i./ha] | Activity [%] against *Polygonum convolvulus* |
|---|---|---|
| A1-74 | 3 | 0 |
| pinoxaden | 10 | 0 |
| A1-74 + pinoxaden | 3 + 10 | 30 ($E^C$ = 0, Δ = 30) |

TABLE 5-89

Greenhouse

| Active compound | Dosage [g of a.i./ha] | Activity [%] against *Veronica hederifolia* |
|---|---|---|
| A1-74 | 3 | 40 |
| pinoxaden | 10 | 20 |
| A1-74 + pinoxaden | 3 + 10 | 60 ($E^C$ = 52, Δ = 8) |

TABLE 5-90

Greenhouse

| Active compound | Dosage [g of a.i./ha] | Activity [%] against *Bidens pilosa* |
|---|---|---|
| A1-79 | 2 | 20 |
| imazamox | 1 | 10 |
| A1-79 + imazamox | 2 + 1 | 55 ($E^C$ = 28, Δ = 27) |

TABLE 5-91

Greenhouse

| Active compound | Dosage [g of a.i./ha] | Activity [%] against *Ambrosia artemisiifolia* |
|---|---|---|
| A1-79 | 2 | 30 |
| imazamox | 2 | 10 |
| A1-79 + imazamox | 2 + 2 | 70 ($E^C$ = 37, Δ = 33) |

TABLE 5-92

Field

| Active compound | Dosage [g of a.i./ha] | Activity [%] against *Galium aparine* |
|---|---|---|
| A1-79 | 25 | 70 |
| bromoxynil | 210 | 25 |
| A1-79 + bromoxynil | 25 + 210 | 90 ($E^C$ = 78, Δ = 12) |

TABLE 5-93

Greenhouse

| Active compound | Dosage [g of a.i./ha] | Activity [%] against *Ambrosia artemisiifolia* |
|---|---|---|
| A1-80 | 1 | 25 |
| diflufenzopyr | 25 | 50 |
| A1-80 + diflufenzopyr | 1 + 25 | 85 ($E^C$ = 63, Δ = 23) |

TABLE 5-94

Greenhouse

| Active compound | Dosage [g of a.i./ha] | Activity [%] against *Brachiaria platyphylla* |
|---|---|---|
| A1-81 | 1 | 10 |
| dicamba | 12.5 | 0 |
| A1-81 + dicamba | 1 + 12.5 | 40 ($E^C$ = 10, Δ = 30) |

TABLE 5-95

Greenhouse

| Active compound | Dosage [g of a.i./ha] | Activity [%] against *Echinochloa crus-galli* |
|---|---|---|
| A1-81 | 1 | 10 |
| dicamba | 12.5 | 0 |
| A1-81 + dicamba | 1 + 12.5 | 40 ($E^C$ = 10, Δ = 30) |

TABLE 5-96

Greenhouse

| Active compound | Dosage [g of a.i./ha] | Activity [%] against *Bidens pilosa* |
|---|---|---|
| A1-83 | 1 | 35 |
| thiencarbazone-methyl | 0.5 | 40 |
| A1-83 + thiencarbazone-methyl | 1 + 0.5 | 75 ($E^C$ = 61, Δ = 14) |

TABLE 5-97

Greenhouse

| Active compound | Dosage [g of a.i./ha] | Activity [%] against *Brachiaria platyphylla* |
|---|---|---|
| A1-83 | 0.5 | 0 |
| thiencarbazone-methyl | 0.5 | 75 |
| A1-83 + thiencarbazone-methyl | 0.5+ 0.5 | 85 ($E^C$ = 75, Δ = 10) |

TABLE 5-98

Greenhouse

| Active compound | Dosage [g of a.i./ha] | Activity [%] against *Pharbitis purpurea* |
|---|---|---|
| A1-84 | 2 | 30 |
| imazamox | 1 | 15 |
| A1-84 + imazamox | 2+ 1 | 70 ($E^C$ = 41, Δ = 30) |

TABLE 5-99

Greenhouse

| Active compound | Dosage [g of a.i./ha] | Activity [%] against *Xanthium strumarium* |
|---|---|---|
| A1-84 | 1 | 10 |
| imazamox | 1 | 0 |
| A1-84 + imazamox | 1 + 1 | 40 ($E^C$ = 10, Δ = 30) |

TABLE 5-100

Greenhouse

| Active compound | Dosage [g of a.i./ha] | Activity [%] against *Ambrosia artemisiifolia* |
|---|---|---|
| A1-85 | 1 | 50 |
| imazamox | 1 | 0 |
| A1-85 + imazamox | 1 + 1 | 70 ($E^C$ = 50, Δ = 20) |

TABLE 5-101

Greenhouse

| Active compound | Dosage [g of a.i./ha] | Activity [%] against *Xanthium strumarium* |
|---|---|---|
| A1-85 | 1 | 25 |
| imazamox | 1 | 10 |
| A1-85 + imazamox | 1 + 1 | 50 ($E^C$ = 33, Δ = 18) |

TABLE 5-102

Greenhouse

| Active compound | Dosage [g of a.i./ha] | Activity [%] against *Ambrosia artemisiifolia* |
|---|---|---|
| A2-4 | 1 | 40 |
| imazamox | 2 | 0 |
| A2-4 + imazamox | 1 + 2 | 60 ($E^C$ = 40, Δ = 20) |

TABLE 5-103

Greenhouse

| Active compound | Dosage [g of a.i./ha] | Activity [%] against *Xanthium strumarium* |
|---|---|---|
| A2-4 | 2 | 10 |
| imazamox | 2 | 0 |
| A2-4 + imazamox | 2 + 2 | 35 ($E^C$ = 10, Δ = 25) |

TABLE 5-104

| | Field | |
|---|---|---|
| Active compound | Dosage [g of a.i./ha] | Activity [%] against *Euphorbia heterophylla* |
| A2-4 | 25 | 50 |
| atrazine | 1000 | 55 |
| A2-4 + atrazine | 25 + 1000 | 93 ($E^C$ = 78, $\Delta$ = 16) |

TABLE 5-105

| | Greenhouse | |
|---|---|---|
| Active compound | Dosage [g of a.i./ha] | Activity [%] against *Brachiaria platyphylla* |
| A2-9 | 1 | 0 |
| dicamba | 12.5 | 0 |
| A2-4 + imazamox | 1 + 12.5 | 15 ($E^C$ = 0, $\Delta$ = 15) |

TABLE 5-106

| | Greenhouse | |
|---|---|---|
| Active compound | Dosage [g of a.i./ha] | Activity [%] against *Digitaria sanguinalis* |
| A2-9 | 2 | 65 |
| dicamba | 12.5 | 0 |
| A2-9 + dicamba | 2 + 12.5 | 85 ($E^C$ = 65, $\Delta$ = 20) |

TABLE 5-108

| | Greenhouse | |
|---|---|---|
| Active compound | Dosage [g of a.i./ha] | Activity [%] against *Echinochloa crus-galli* |
| A2-9 | 1 | 0 |
| dicamba | 12.5 | 0 |
| A2-9 + dicamba | 1 + 12.5 | 15 ($E^C$ = 0, $\Delta$ = 15) |

TABLE 5-109

| | Greenhouse | |
|---|---|---|
| Active compound | Dosage [g of a.i./ha] | Activity [%] against *Brachiaria platyphylla* |
| A2-10 | 2 | 0 |
| lenacil | 4 | 0 |
| A2-10 + lenacil | 2 + 4 | 25 ($E^C$ = 0, $\Delta$ = 25) |

TABLE 5-110

| | Greenhouse | |
|---|---|---|
| Active compound | Dosage [g of a.i./ha] | Activity [%] against *Brachiaria platyphylla* |
| A2-10 | 1 | 35 |
| lenacil | 4 | 0 |
| A2-10 + lenacil | 1 + 4 | 65 ($E^C$ = 35, $\Delta$ = 30) |

TABLE 5-111

| | Greenhouse | |
|---|---|---|
| Active compound | Dosage [g of a.i./ha] | Activity [%] against *Bidens pilosa* |
| A2-10 | 2 | 50 |
| lenacil | 4 | 0 |
| A2-10 + lenacil | 2 + 4 | 80 ($E^C$ = 50, $\Delta$ = 30) |

TABLE 5-112

| | Greenhouse | |
|---|---|---|
| Active compound | Dosage [g of a.i./ha] | Activity [%] against *Setaria viridis* |
| A3-7 | 2 | 0 |
| diflufenzopyr | 12.5 | 50 |
| A3-7 + diflufenzopyr | 2 + 12.5 | 70 ($E^C$ = 50, $\Delta$ = 20) |

TABLE 5-113

| | Greenhouse | |
|---|---|---|
| Active compound | Dosage [g of a.i./ha] | Activity [%] against *Brachiaria platyphylla* |
| A4-2 | 1 | 0 |
| diflufenzopyr | 25 | 60 |
| A4-2 + diflufenzopyr | 1 + 25 | 75 ($E^C$ = 60, $\Delta$ = 15) |

TABLE 5-114

| | Field | |
|---|---|---|
| Active compound | Dosage [g of a.i./ha] | Activity [%] against *Stellaria media* |
| A4-2 | 25 | 63 |
| bromoxynil | 210 | 10 |
| A4-2 + bromoxynil | 25 + 210 | 90 ($E^C$ = 67, $\Delta$ = 23) |

TABLE 5-115

| | Greenhouse | |
|---|---|---|
| Active compound | Dosage [g of a.i./ha] | Activity [%] against *Echinochloa crus-galli* |
| A4-7 | 3 | 50 |
| dicamba | 12.5 | 0 |
| A4-7 + dicamba | 3 + 12.5 | 65 ($E^C$ = 50, $\Delta$ = 15) |

TABLE 5-116

| | Field | |
|---|---|---|
| Active compound | Dosage [g of a.i./ha] | Activity [%] against *Stellaria media* |
| A4-7 | 25 | 60 |
| bromoxynil | 210 | 5 |
| A4-7 + bromoxynil | 25 + 210 | 88 ($E^C$ = 62, $\Delta$ = 26) |

The invention claimed is:

1. A herbicidal composition comprising
(A) a compound of formula (I) and/or salts thereof

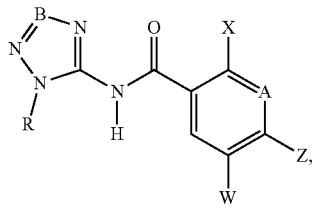

(I)

in which
A represents CY,
B represents N,
X represents chlorine,
Y represents SCH$_3$,
Z represents trifluoromethyl,
W represents hydrogen,
R represents methyl
and
(B) one or more organic phosphorus compounds selected from the group consisting of glyphosate, glyphosate-isopropyl-ammonium, glyphosate-ammonium, glyphosate-trimesium (sulfosate), glyphosate-diammonium, and glyphosate-potassium,
wherein component (A) and component (B) are present in synergistically effective amounts.

2. The herbicidal composition as claimed in claim 1 additionally comprising, as component C, one or more safeners selected from the group consisting of benoxacor, cloquintocet-mexyl, cyprosulfamide, dichlormid, fenclorim, fenchlorazole, furilazole, isoxadifen-ethyl, mefenpyr-diethyl, 4-(dichloroacetyl)-1-oxa-4-azaspiro[4.5]decane, and 2,2,5-trimethyl-3-(dechloroacetyl)-1,3-oxazolidine.

3. The herbicidal composition as claimed in claim 1 comprising as

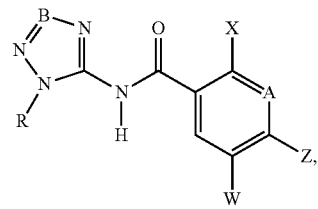

(I)

(B) glyphosate or glyphosate-isopropyl-ammonium.

4. A method for controlling harmful plants in crops, comprising applying a herbicidally active amount of a herbicidal composition as claimed in claim 1 to one or more harmful plants, one or more plant parts, one or more plant seeds and/or an area on which a plant grows.

5. The method as claimed in claim 4, wherein the crop is selected from the group consisting of sugar cane, corn, wheat, rye, barley, oats, rice, sorghum, cotton and soybean.

6. The method as claimed in claim 4, wherein the crop has been genetically modified.

7. A method for controlling harmful plants in crops comprising applying to one or more harmful plants, one or more plant parts, one or more plant seeds and/or an area on which a plant grows, a herbicidal composition as claimed in claim 1 comprising
(A) one or more compounds of formula (I) and/or salts thereof at an application rate of 3 to 200 g/ha, and
(B) one or more organic phosphorus compounds at an application rate of 3 to 2000 g/ha.

8. The method of claim 7 additionally comprising (C) one or more safeners selected from the group consisting of benoxacor, cloquintocet-mexyl, cyprosulfamide, dichlormid, fenclorim, fenchlorazole, furilazole, isoxadifen-ethyl, mefenpyr-diethyl, 4-(dichloroacetyl)-1-oxa-4-azaspiro[4.5]decane, and 2,2,5-trimethyl-3-(dechloroacetyl)-1,3-oxazolidine applied at an application rate of 1 to 500 g/ha.

* * * * *